United States Patent
Lu et al.

(10) Patent No.: US 9,745,348 B2
(45) Date of Patent: Aug. 29, 2017

(54) SHORT DESIGNED PEPTIDES POSSESSING SELECTIVE ACTIONS AGAINST BACTERIA AND CANCER CELLS

(71) Applicant: The University of Manchester, Manchester (GB)

(72) Inventors: Jian R. Lu, Altrincham (GB); Xiubo Zhao, Manchester (GB); Fang Pan, Manchester (GB); Mohammed Yaseen, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 14/204,814

(22) Filed: Mar. 11, 2014

(65) Prior Publication Data
US 2015/0057217 A1   Feb. 26, 2015

Related U.S. Application Data

(63) Continuation of application No. PCT/GB2012/052279, filed on Sep. 14, 2012.

(30) Foreign Application Priority Data

Sep. 14, 2011 (GB) .................... 1115910.0

(51) Int. Cl.
| | | |
|---|---|---|
| C07K 7/06 | (2006.01) |
| A61K 38/00 | (2006.01) |
| C07K 7/08 | (2006.01) |
| C07K 14/00 | (2006.01) |

(52) U.S. Cl.
CPC .................. *C07K 7/08* (2013.01); *C07K 7/06* (2013.01); *C07K 14/001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,789,381 A | 8/1998 | Cochrane et al. |
| 7,001,983 B1 | 2/2006 | Shai et al. |
| 2005/0215481 A1 | 9/2005 | Kim et al. |
| 2011/0294722 A1 | 12/2011 | Durner et al. |

FOREIGN PATENT DOCUMENTS

| | | | |
|---|---|---|---|
| DE | EP 2 168 976 | * | 3/2010 |
| EP | 2168976 A1 | | 3/2010 |
| KR | 2003-0061718 A | | 7/2003 |
| WO | WO-95/00547 A1 | | 1/1995 |
| WO | WO-96/28468 A2 | | 9/1996 |
| WO | WO-98/37090 A1 | | 8/1998 |
| WO | WO-01/10887 A2 | | 2/2001 |
| WO | WO-01/12668 A1 | | 2/2001 |
| WO | WO-01/83522 A2 | | 11/2001 |
| WO | WO-02/00839 A2 | | 1/2002 |
| WO | WO-02/16593 A2 | | 2/2002 |
| WO | WO-03/006043 A1 | | 1/2003 |
| WO | WO-03/080652 A1 | | 10/2003 |
| WO | WO-2008/057158 A2 | | 5/2008 |

OTHER PUBLICATIONS

Cerovsky et al., ChemBioChem, 2009, 10, 2089-99.*
Chen, C. et al., "High Cell Selectivity and Low-Level Antibacterial Resistance of Designed Amphiphilic Peptide G(IIKK)₃I-NH₂," ACS Applied Materials and Interfaces, vol. 6, pp. 16529-16536 (2014).
Chen, C. et al., "High Selective Performance of Designed Antibacterial and Anticancer Peptide Amphiphiles," ACS Applied Materials and Interfaces, vol. 7, pp. 17346-17355 (2015).
Chen, C. et al., "Molecular mechanisms of anticancer action and cell selectivity of short α-helical peptides," Biomaterials, vol. 35, pp. 1552-1561 (2014).
Hu, J. et al., "Designed Antimicrobial and Antitumor Peptides with High Selectivity," BioMacromolecules, vol. 12, pp. 3839-3843 (2011).
Asthana, N. et al., "Dissection of antibacterial and toxic activity of melittin: a leucine zipper motif plays a crucial role in determining its hemolytic activity but not antibacterial activity," J. Biol. Chem., vol. 279, No. 53, pp. 55042-55050 (Dec. 31, 2004).
Braunstein, A. et al., "In vitro activity and potency of an intravenously injected antimicrobial peptide and its DL amino acid analog in mice infected with bacteria," Antimicrob. Agents Chemother., vol. 48, No. 8, pp. 3127-3129 (Aug. 2004).

(Continued)

*Primary Examiner* — James H Alstrum Acevedo
*Assistant Examiner* — Roy Teller
(74) *Attorney, Agent, or Firm* — Wilmer Cutler Pickering Hale and Dorr LLP

(57) ABSTRACT

The present invention relates to amphiphilic peptides having antibacterial and/or antitumor activity, and to therapeutic and non-therapeutic compositions comprising these peptides. The peptides are of structural formula I or II shown below

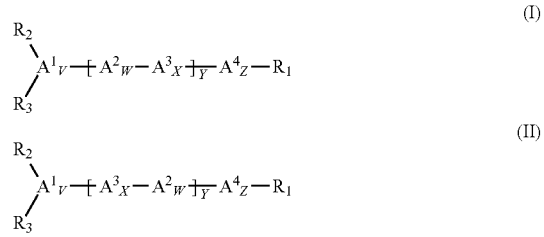

wherein $A^1$, v, $A^2$, w, $A^3$, x, y, $A^4$, z, $R_1$, $R_2$ and $R_3$ are as defined in the application;
or a salt thereof. The invention further relates to use of the peptides as antibacterial agents, or antitumor agents, including the medical use of the peptide in treating infection and/or cancer, as well as their use as preservatives and antibacterial agents in other products, including personal care products such as skin topical treatments, cleansers, mouth washes, toothpastes, shampoo, body lotions and creams etc.

21 Claims, 18 Drawing Sheets

(56) References Cited

OTHER PUBLICATIONS

Cerovsky, V. et al., "Lasioglossins: Three Novel Antimicrobial Peptides from the Venom of the Eusocial Bee Lasioglossum laticeps (Hymenoptera: Halictidae)," Chembiochem, vol. 10, No. 12, pp. 2089-2099 (Aug. 17, 2009).
Cruciani, R. A. et al., "Antibiotic magainins exert cytolytic activity against transformed cell lines through channel formation," Proc. Natl. Acad. Sci. USA, vol. 88, No. 9, pp. 3792-3796 (May 1, 1991).
Dathe, M. et al., "Optimization of the antimicrobial activity of magainin peptides by modification of charge," FEBS Letters, vol. 501, No. 2-3, pp. 146-150 (Jul. 20, 2001).
De Groote, D. et al., "Direct stimulation of cytokines (IL-1β, TNF-α, IL-6, IL-2, IFN-γ and GM-CSF) in whole blood. I. Comparison with isolated PBMC stimulation," Cytokine, vol. 4, No. 3, pp. 239-248 (May 1992).
Feghali, C. A. et al., "Cytokines in Acute and Chronic Inflammation," Frontiers in Bioscience, vol. 2, pp. d12-d26 (Jan. 1, 1997).
Greenwood, D and O'Grady, F., "Differential Effects of Benzylpenicillin and Ampicillin on *Escherichia coli* and Proteus mirabilis in Conditions Simulating Those of the Urinary Bladder," J. Infect. Dis., vol. 122, No. 6, pp. 465-471 (Dec. 1970).
Hu, J. et al., "Designed antimicrobial and antitumor peptides with high selectivity," Biomacromolecules, vol. 12, No. 11, pp. 3839-3843 (Nov. 14, 2011).
International Search Report and Written Opinion issued by the European Patent Office as International Searching Authority for International Application No. PCT/GB2012/052279 dated Dec. 13, 2012 (14 pages).
Jullian, M. et al., "N-terminus FITC labeling of peptides on solid support: the truth behind the spacer," Tetrahedron Letters, vol. 50, No. 3, pp. 260-263 (Jan. 21, 2009).
No Author Listed, "Pathogenic bacteria," Wikipedia, the free encyclopedia, retrieved from the internet: URL<https://en.wikipedia.org/wiki/Pathogenic_bacteria>, 10 pages (retrieved on Jun. 25, 2015).
Papo, N. and Shai, Y., "Visions & Reflections: Host defense peptides as new weapons in cancer treatment," Cellular and Molecular Life Sciences (CMLS), vol. 62, No. 7-8, pp. 784-790 (Apr. 2005).
Park, H. K. et al., "Influence of the N- and C-terminal regions of leu-lys rich antimicrobial peptide on antimicrobial activity," Protein Pept. Lett., vol. 15, No. 2, pp. 188-192 (2008).
Rand, K. D. and Jorgensen, T. J., "Development of a peptide probe for the occurrence of hydrogen (1H/2H) scrambling upon gas-phase fragmentation," Anal. Chem., vol. 79, No. 22, pp. 8686-8693 (Nov. 15, 2007).
Takara, K. et al., "Molecular changes to HeLa cells on continuous exposure to cisplatin or paclitaxel," Cancer Chemother. Pharmacol., vol. 58, No. 6, pp. 785-793 (Dec. 2006).
Tossi, A. et al., "Amphipathic, alpha-helical antimicrobial peptides," Biopolymers, vol. 55, No. 1, pp. 4-30 (2000).
Tossi, A. et al., "Design of Synthetic Antimicrobial Peptides Based on Sequence Analogy and Amphipathicity," European Journal of Biochemistry, vol. 250, No. 2, pp. 549-558 (Dec. 1997).
United Kingdom Search Report issued by the Intellectual Property Office of the United Kingdom for Application No. GB1115910.0 dated Jan. 10, 2012 (5 pages).
Wieprecht, T. et al., "Peptide hydrophobicity controls the activity and selectivity of magainin 2 amide in interaction with membranes," Biochemistry, vol. 36, No. 20, pp. 6124-6132 (May 20, 1997).
Wiradharma, N. et al., "Synthetic cationic amphiphilic α-helical peptides as antimicrobial agents," Biomaterials, vol. 32, No. 8, pp. 2204-2212 (Mar. 2011).
Wiradharma, N. et al., "The effect of thiol functional group incorporation into cationic helical peptides on antimicrobial activities and spectra," Biomaterials, vol. 32, No. 34, pp. 9100-9108 (Dec. 2011).
Chen et al., "Amino acid side chains affect the bioactivity of designed short peptide amphiphiles," Journal of Materials Chemistry B, The Royal Society of Chemistry, vol. 4, pp. 2359-2368, (2016).
Wiegand et al., "Agar and broth dilution methods to determine the minimal inhibitory concentration (MIC) of antimicrobial substances," Nature Protocols, vol. 3, No. 2, pp. 163-175, (2008).
Chen et al., "Surface Physical Activity and Hydrophobicity of Designed Helical Peptide Amphiphiles Control Their Bioactivity and Cell Selectivity", ACS Applied Materials & Interfaces, vol. 8, No. 40, pp. 26501-26510, published online Sep. 19, 2016.

* cited by examiner

| Peptides | MIC (µM) | | IC$_{50}$ (µM) | | EC$_{50}$ (µM) |
|---|---|---|---|---|---|
| | E.coli | | HeLa | | |
| | B.Subtilis | | HL60 | | |
| G(IIKK)I | - | | - | - | - |
| G(IIKK)$_2$I | 130±5 | | 160±7 | | - |
| | 28±3 | | >500 | | |
| G(IIKK)$_3$I | 9±1 | | 15±5.0 | | >250 |
| | 2±1 | | 25±5.0 | | |
| G(IIKK)$_4$I | 2±0.5 | | 4±2.5 | 10±2.5 | 36±2 |
| | 0.5±0.2 | | | | |
| G(LLKK)$_3$L | 7±0.5 | | 10±2.5 | | 28±3 |
| | 2±0.5 | | 8±2.5 | | |
| G(VVKK)$_3$V | 125±10 | | 70±10 | | >600 |
| | 65±5 | | >100 | | |
| G(IIOO)$_3$I | 3±0.5 | | 3±1.0 | | >250 |
| | 1.5±0.5 | | 5±2.0 | | |
| GKI(KKII)$_2$KII | 2±0.5 | | 16±3 | | 150 |
| | 1±0.5 | | 10±2 | | |
| GIK(KKII)$_2$KII | 3±0.5 | | 50±10 | | >250 |
| | 1±0.5 | | 10±2.5 | | |
| Magainin-2[a] | 38 | >80 | >60 | - | 430 |
| Melittin[b] | 3.9±0.6 | | - | - | 3 |
| | 2.0±0.2 | | | | |
| Ampicillin[c] | ~11 | 5.5 | - | - | - |
| Cisplatin[d] | - | - | 1.34±0.32 | - | - |

Figure 7 (Table 3)

SHORT DESIGNED PEPTIDES POSSESSING SELECTIVE ACTIONS AGAINST BACTERIA AND CANCER CELLS

CROSS-REFERENCE TO RELATED PATENT APPLICATIONS

This application is a continuation of International Application No. PCT/GB2012/052279, filed Sep. 14, 2012, which claims the benefit of priority to Great Britain Application No. GB 1115910.0, filed Sep. 14, 2011, both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Oct. 10, 2014, is named 2206057.00125US1_SL.txt and is 12,051 bytes in size.

FIELD OF THE INVENTION

The invention relates to amphiphilic peptides having antibacterial and/or antitumor activity, and to therapeutic and non-therapeutic compositions comprising these peptides. The invention further relates to use of the peptides as antibacterial agents, or antitumor agents, including the medical use of the peptide in treating infection and/or cancer, as well as their use as preservatives and antibacterial agents in other products, including personal care products such as skin topical treatments, cleansers, mouth washes, toothpastes, shampoo, body lotions and creams etc.

BACKGROUND OF THE INVENTION

There is a need for new and effective antibacterial agents, antibacterial agents that can be used for therapeutic applications.

Antibiotic resistance is a phenomenon that is becoming increasingly difficult to address. The recent emergence and spread of NDM-1 (New Delhi metallo-β-lactamase-1) producing bacteria, resistant to many groups of antibiotics including the powerful β-lactams (e.g. carbapenems), has led to infection spreading across many countries. The global panic has again fueled the urgent need to discover novel bactericidal agents for therapeutic purposes.

Antimicrobial peptides (AMPs) are the evolutionarily conserved effectors in innate immunity. Their broad-spectral bactericidal activity, rapid killing rate, and the distinctive mode of action (i.e. targeting the bacterial cell membrane itself rather than specific receptors such as proteins and DNA), have made them promising candidates for the development of alternative agents to cope with the widespread challenges of bacterial resistance. However, although over 1000 AMPs have been isolated and characterized from different sources, only limited success has so far been achieved in clinical trials. The major barriers for converting the peptides into drugs lie in the high cost of production on a large scale, toxicity to host cells, and susceptibility to proteolytic degradation. Furthermore, concerns have recently emerged from the clinical use of AMPs with sequences that are too close to those of natural human AMPs, relating to the inevitable compromise of human natural defense, thereby imposing possible threats to public health.

Accordingly there remains a need for new, and effective antimicrobial agents, that are clinically useful.

In addition, there is also a need for effective and inexpensive antibacterial agents that can be used either as preservatives or antibacterial agents in personal care compositions (such as antibacterial creams, ointments, lotions, shampoos, hand washes, mouthwashes, toothpastes etc.). Many preservatives and antibacterial agents used are synthetic chemicals that suffer from poor biocompatibility.

It is an objective of the present invention to provide a range of antibacterial amphiphilic peptides that are of use as personal care products and as potential therapeutic agents.

SUMMARY OF THE INVENTION

AMPs are highly diverse in terms of length, sequence and structure, making it challenging to design short and efficient sequences. However, the inventors have successfully devised a series of short, amphiphilic peptides that can kill gram-positive and gram-negative bacteria as effectively as several well known antimicrobial peptides and antibiotics. For example, the inventors have demonstrated that peptides of formula $G(IIKK)_nI\text{-}NH_2$ (n=3-4) (SEQ ID NO: 22) described herein display bactericidal activity against both gram-positive and gram-negative bacteria with minimum inhibitory concentrations (MICs) around 0.5-8 µM.

In addition to antimicrobial activity, some of the peptides have been shown to possess potent antitumor activities against cancer cell lines. For example, the $G(IIKK)_nI\text{-}NH_2$ (n=3-4) peptides (SEQ ID NO: 22) have been shown to be effective against two selected cancer cell lines with 50% growth inhibition concentrations ($IC_{50}$) around 4-25 µM.

Still further, the cytotoxicity of the present peptides, determined from lysis of human erythrocyte cells, remains remarkably low at values up to 10-fold MICs or much greater. The $G(IIKK)_3I\text{-}NH_2$ peptide (SEQ ID NO: 3) described herein has further been shown to have a rapid and high selectivity to microbes or tumor cells (HL60 cancer cell line) with minimal cytotoxicity to model host cells (3T3 cell line and primary human dermal fibroblast cells) when co-cultured in vitro.

Thus the invention provides new peptides which demonstrate selective activity against bacteria and/or cancer cells, without endangering normal host cells. Furthermore, the peptides also have a relatively small size and simple composition that favours low manufacturing costs and easy quality control. The peptides thus offer new opportunities in the development of cost effective and highly selective antimicrobial agents for use in the personal care products, as preservatives and in antibacterial and antitumor treatments.

Accordingly, in one aspect the invention provides an amphiphilic peptide of formula I or II, or a salt thereof, as defined herein.

In another aspect the invention provides a method of synthesising an amphiphilic peptide of formula I or II, or a salt thereof, as defined herein.

In another aspect the invention provides a composition comprising an amphiphilic peptide of formula I or II, or a salt thereof, as defined herein. The composition may be a pharmaceutical composition, a disinfectant composition, or a personal care composition as defined herein.

In another aspect the invention provides the use of an amphiphilic peptide of formula I or II, or a salt thereof, as defined herein as a surfactant.

In another aspect the invention provides the use of an amphiphilic peptide of formula I or II, or a salt thereof, as defined herein as a preservative.

In another aspect the invention provides the use of an amphiphilic peptide of formula I or II, or a salt thereof, as defined herein as an antibacterial agent.

In another aspect the invention provides an amphiphilic peptide of formula I or II, or a pharmaceutically acceptable salt thereof, as defined herein for use as a medicament.

In another aspect the invention provides an amphiphilic peptide of formula I or II, or a pharmaceutically acceptable salt thereof, as defined herein for use in the treatment of a bacterial infection.

In another aspect the invention provides a method of treating a bacterial infection in an individual in need of such treatment, the method comprising administering a therapeutically effective amount of an amphiphilic peptide of formula I or II, or a pharmaceutically acceptable salt thereof, as defined herein.

In another aspect the invention provides an amphiphilic peptide of formula I or II, or a pharmaceutically acceptable salt thereof, as defined herein for use in the treatment of cancer.

In another aspect the invention provides a method of treating cancer in an individual in need of such treatment, the method comprising administering a therapeutically effective amount of an amphiphilic peptide of formula I or II, or a pharmaceutically acceptable salt thereof, as defined herein.

BRIEF DESCRIPTION OF THE DRAWINGS

FIGS. 2A and 2B disclose SEQ ID NOS 1-4, respectively, in order of appearance.

FIG. 3—CD spectra of peptides 1-4 (the G(IIKK)$_n$I-NH$_2$ (n=1-4) (SEQ ID NO: 23) series) in aqueous phase (A) containing, 0.5 mg/ml DPPC small unilamellar vesicles (SUVs) in 10 mM Tris buffer (B), and 0.5 mg/ml DPPG SUVs in 10 mM Tris buffer (C). The concentrations of peptides were maintained at 0.1 mM.

FIG. 4—Survival rate curves for *E. coli* DH5α (A) and *B. subtilis* 168 (B) bacteria in the presence of varying concentrations of peptides 1-4. Controls were bacteria without peptide.

FIG. 5—Survival rate curves for HeLa (A) and HL60 (B) cells in the presence of varying concentrations of peptides 1-4. Curves were obtained using MTT assays as described herein.

FIGS. 6A and 6B disclose SEQ ID NOS 1-4, and 3, 8 and 5, respectively, in order of appearance.

FIG. 7—(Table 3) Bioactivities and cytotoxicities of peptides 1-9 (SEQ ID NOS 1-9, respectively, in order of appearance), with two natural antibacterial peptides, antibiotic ampicillin and anticancer drug Cisplatin cited for comparison. MIC: the lowest peptide/drug concentration to inhibit bacterial growth; IC$_{50}$: concentration causing 50% tumor cell growth inhibition and EC$_{50}$: concentration to induce 50% lysis of erythrocytes. ([a]—cited from Dathe et al 2001, Cruciani et al 1991, Wieprecht et al 1997; [b]—cited from Asthana et al 2004; [c]—cited from Greenwood et al 1970; [d]—cited from Takara et al 2006)

FIGS. 10A and 10B disclose SEQ ID NOS 1-4, respectively, in order of appearance.

BRIEF DESCRIPTION OF THE SEQUENCES

Figure 1:
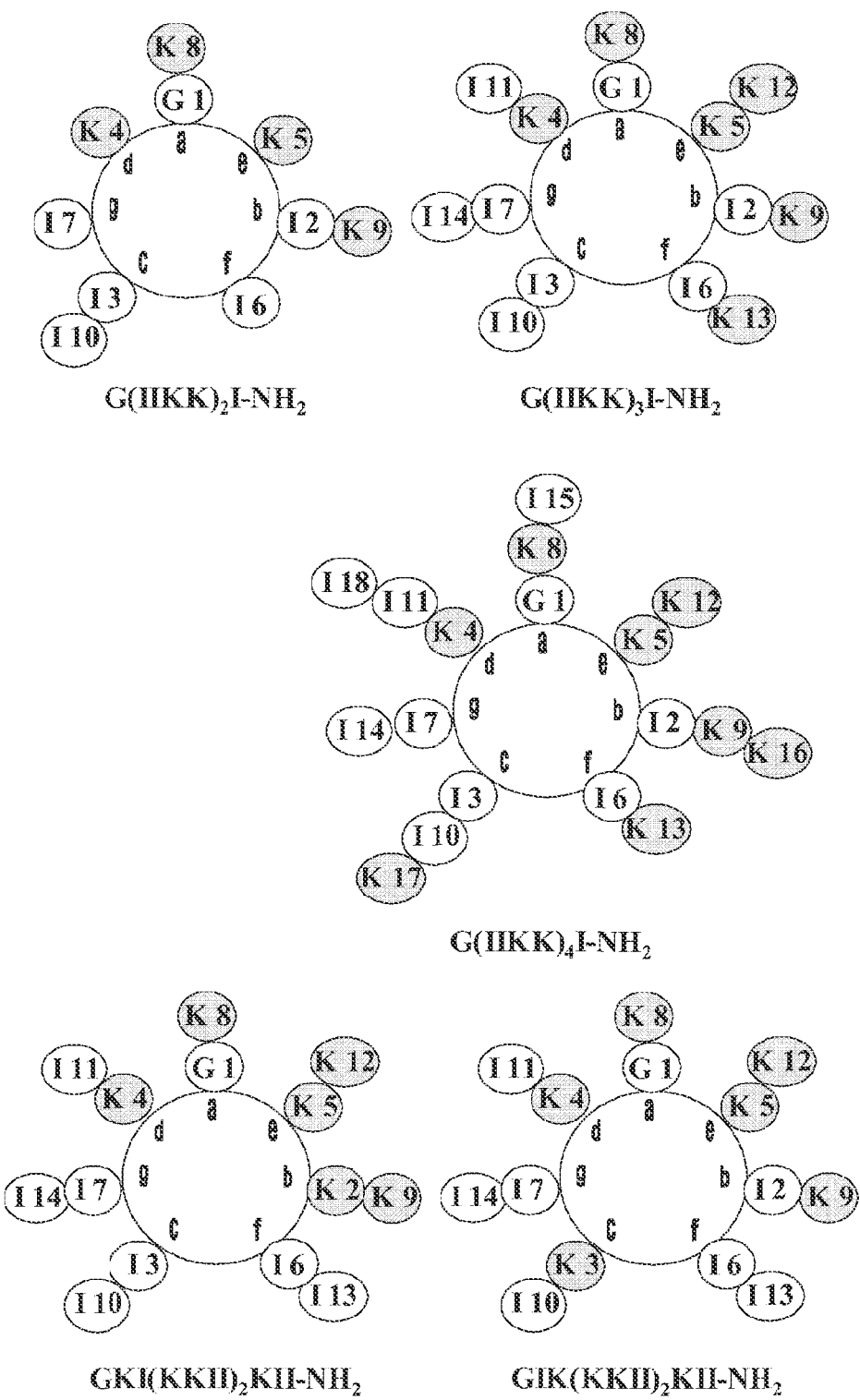
FIG. 1—Schiffer-Edmundson wheel projection of helical peptides 2, 3, 4, 8 and 9 as shown in Table 1 (SEQ ID NOS 2-4 and 8-9, respectively, in order of appearance). Amino acids are represented by one letter code and number (indicating the sequence as appeared in the peptide).

SEQ ID NO: 1 is the amino acid sequence of peptide 1 (helix-1 in Table 1).
SEQ ID NO: 2 is the amino acid sequence of peptide 2 (helix-2 in Table 1).
SEQ ID NO: 3 is the amino acid sequence of peptide 3 (helix-3 in Table 1).
SEQ ID NO: 4 is the amino acid sequence of peptide 4 (helix-4 in Table 1).
SEQ ID NO: 5 is the amino acid sequence of peptide 5 (helix-5 in Table 1).
SEQ ID NO: 6 is the amino acid sequence of peptide 6 (helix-6 in Table 1).
SEQ ID NO: 7 is the amino acid sequence of peptide 7 (helix-7 in Table 1).
SEQ ID NO: 8 is the amino acid sequence of peptide 8 (helix-8 in Table 1).
SEQ ID NO: 9 is the amino acid sequence of peptide 9 (helix-9 in Table 1).
SEQ ID NO: 10 is the nucleotide sequence of a β-actin sense primer described in the Examples.
SEQ ID NO: 11 is the nucleotide sequence of a β-actin antisense primer described in the Examples.
SEQ ID NO: 12 is the nucleotide sequence of an aspase-8 sense primer described in the Examples.
SEQ ID NO: 13 is the nucleotide sequence of an aspase-8 antisense primer described in the Examples.
SEQ ID NO: 14 is the nucleotide sequence of a fas sense primer described in the Examples.
SEQ ID NO: 15 is the nucleotide sequence of a fas antisense primer described in the Examples.
SEQ ID NO: 16 is the nucleotide sequence of a fasL sense primer described in the Examples.
SEQ ID NO: 17 is the nucleotide sequence of a fasL antisense primer described in the Examples.
SEQ ID NO: 18 is the nucleotide sequence of an IL2 sense primer described in the Examples.
SEQ ID NO: 19 is the nucleotide sequence of an IL2 antisense primer described in the Examples.
SEQ ID NO: 20 is the nucleotide sequence of an IL8 sense primer described in the Examples.
SEQ ID NO: 21 is the nucleotide sequence of an IL8 antisense primer described in the Examples.

DETAILED DESCRIPTION OF THE INVENTION

Terminology

Unless otherwise stated, the following terms used in the specification and claims have the following meanings set out below.

It is to be appreciated that references to "preventing" or "prevention" relate to prophylactic treatment and includes preventing or delaying the appearance of clinical symptoms of the state, disorder or condition developing in a human that may be afflicted with or predisposed to the state, disorder or condition but does not yet experience or display clinical or subclinical symptoms of the state, disorder or condition.

It will be appreciated that references to "treatment" or "treating" of a state, disorder or condition includes: (1) inhibiting the state, disorder or condition, i.e., arresting, reducing or delaying the development of the disease or a relapse thereof (in case of maintenance treatment) or at least one clinical or subclinical symptom thereof, (2) relieving or attenuating the disease, i.e. causing regression of the state, disorder or condition or at least one of its clinical or subclinical symptoms or (3) prophylactic treatment.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "pharmaceutically acceptable" is used herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

All publications, patents and patent applications mentioned in this specification are herein incorporated by reference in to the specification to the same extent as if each individual publication, patent or patent application was specifically and individually indicated to be incorporated herein by reference.

The nomenclature used herein to define peptides is that typically used in the art wherein the amino group at the N-terminus appears to the left and the carboxyl group at the C-terminus appears to the right. An amino acid as referred to herein may comprise a naturally occurring amino acid or a synthetic amino acid. Where an amino acid has isomeric forms, in one aspect it is the L-form that is referred to.

In general, an amino acid has the structure of NH$_2$—C(R)(R')—COOH, wherein R and R' each is, independently, hydrogen or the side chain of an amino acid (e.g., R=CH$_3$ and R'=H for Ala), or R and R' may be joined to form a ring system. When included in a peptide described herein therefore, an amino acid other than the N-terminal amino acid, generally has the structure of —NH—C(R)(R')—CO—.

The three letter and single letter codes for referring to naturally occurring amino acids are well known in the art, and are used herein, as below:

| Amino acid | Three letter code | Single letter code |
| --- | --- | --- |
| Alanine | Ala | A |
| Isoleucine | Ile | I |
| Leucine | Leu | L |

| Amino acid | Three letter code | Single letter code |
| --- | --- | --- |
| Valine | Val | V |
| Phenylalanine | Phe | F |
| Tryptophan | Trp | W |
| Tyrosine | Tyr | Y |
| Asparagine | Asn | N |
| Cysteine | Cys | C |
| Glutamine | Gln | Q |
| Methionine | Met | M |
| Serine | Ser | S |
| Threonine | Thr | T |
| aspartic acid | Asp | D |
| glutamic acid | Glu | E |
| Arginine | Arg | R |
| Histidine | His | H |
| Lysine | Lys | K |
| Glycine | Gly | G |
| Proline | Pro | P |

A synthetic amino acid is typically one which does not occur in nature. Examples of synthetic amino acids are well known in the art, and are described herein.

Ornithine (O or Orn) as referred to herein generally has the structure:

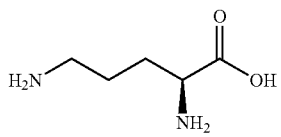

2,3 diamino propionic acid (Dap) as referred to herein generally has the structure:

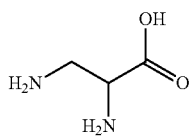

2,4 diamino butyric acid (Dab) as referred to herein generally has the structure:

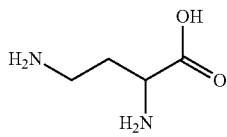

Amphiphilic Peptides

As described above, the present invention is concerned with new amphiphilic peptides, which have a range of different applications as a consequence of, for example, antimicrobial and/or anticancer activity.

In arriving at the invention, the inventors tested various combinations of amphiphilic sequences by aligning hydrophobic and hydrophilic amino acids differently. The inventors initially found that when the peptides contained a simple repeat sequence of IIKK (SEQ ID NO: 24) and the ratio of hydrophobic isoleucine (I) to cationic lysine (K) residues was 1:1, large variations in solution behaviour occurred.

Figure 2:
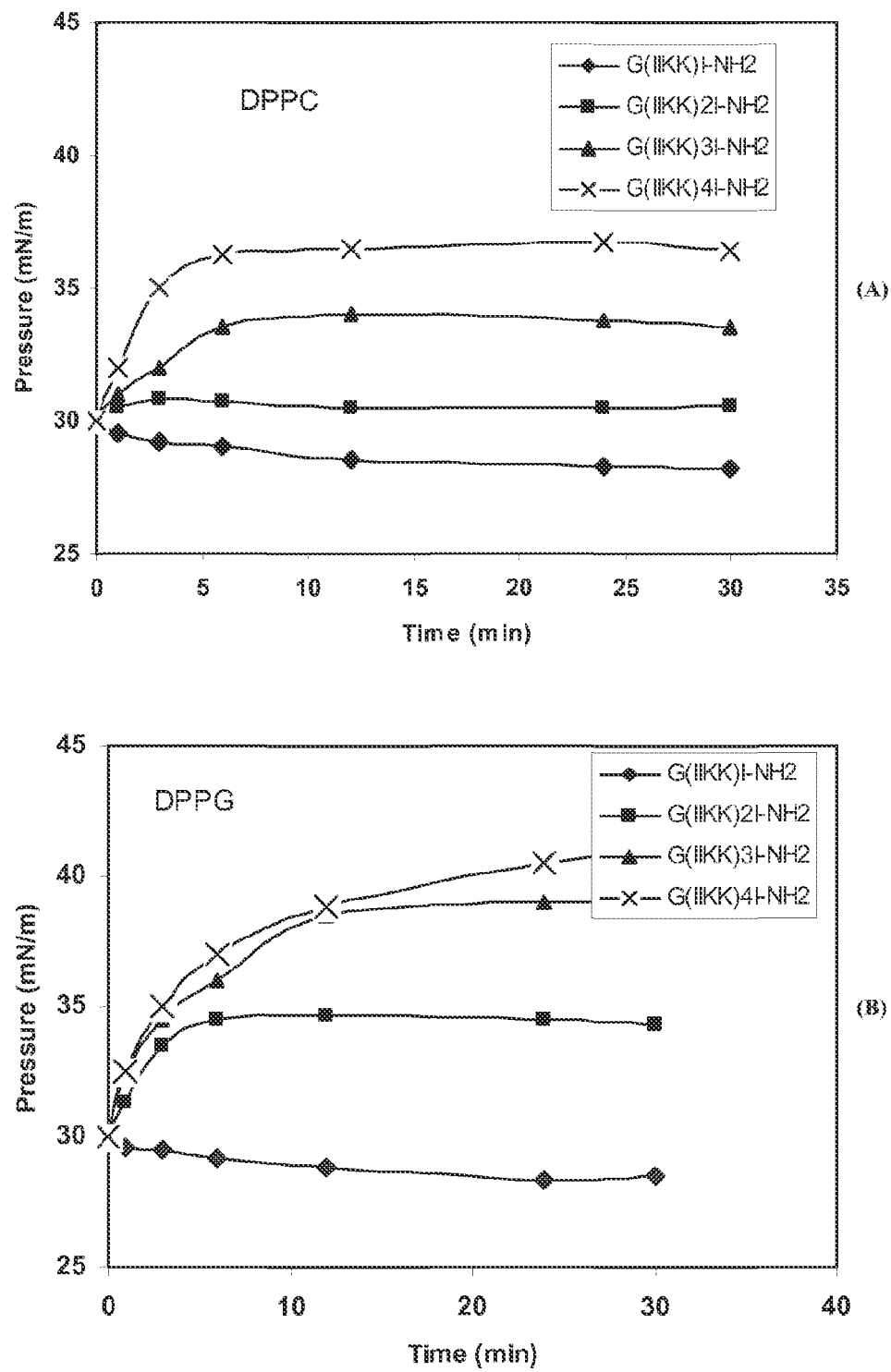
FIG. 2—Graphs showing surface pressure changes over time for DPPC lipid monolayers (A) and DPPG lipid monolayers (B) in the presence of peptides 1-4 (the G(IIKK)$_n$I-NH$_2$ (n=1-4) (SEQ ID NO: 23) series).
Figure 3A:
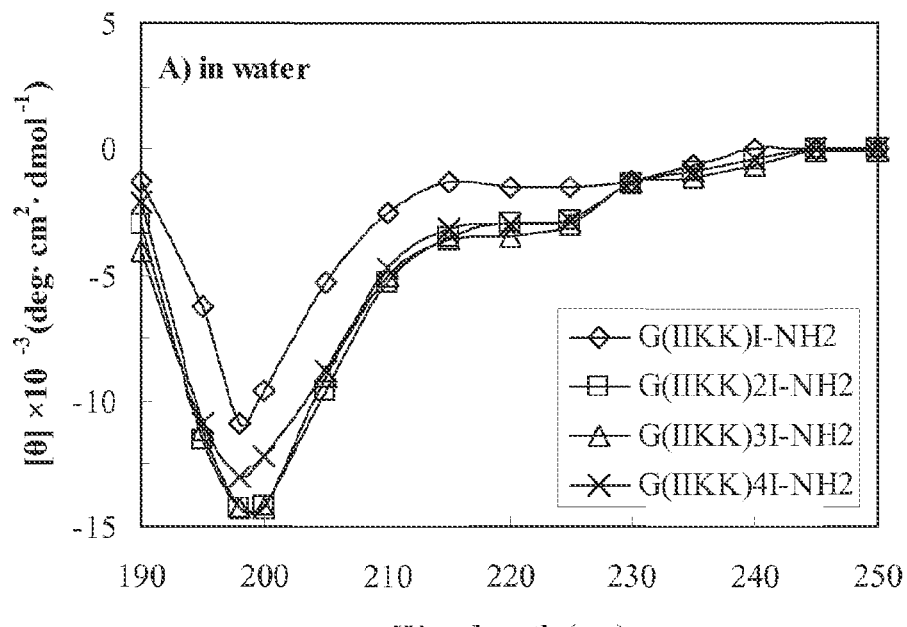
FIGS. 3A, 3B and 3C disclose SEQ ID NOS 1-4, respectively, in order of appearance.

Specifically, the inventors found that peptides, G(IIKK)$_2$I-NH$_2$ (SEQ ID NO: 2), G(IIKK)$_3$I-NH$_2$ (SEQ ID NO: 3) and G(IIKK)$_4$I-NH$_2$ (SEQ ID NO: 4) (peptides 2-4 herein) interact with DPPG lipid monolayers, and on interaction with DPPG vesicles (which are negatively charged and mimic bacterial and tumor cell membranes), undergo a change in secondary structure to form helical structures (Example 1; FIGS. 2 and 3). The peptides do not form such ordered structures in aqueous solution, or in DPPC vesicles (which are zwitterionic, and therefore mimic normal mammalian host cell membranes). This result suggested that a similar structural response might occur on interaction of the peptide with the different cell membrane walls.

Figure 4A:
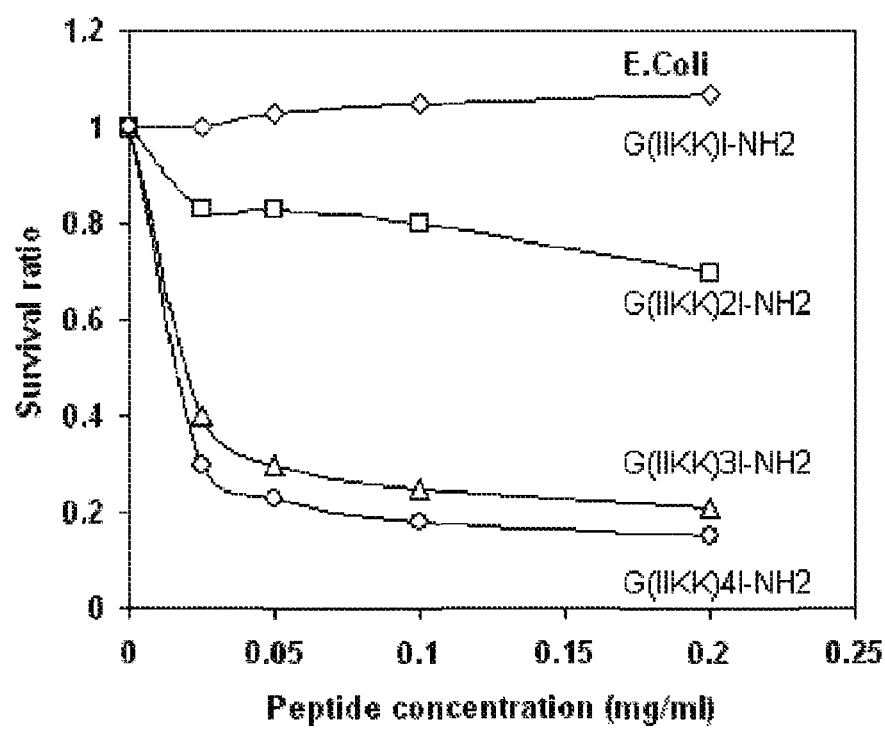
FIGS. 4A and 4B disclose SEQ ID NOS 1-4, respectively, in order of appearance.
Figure 4B:
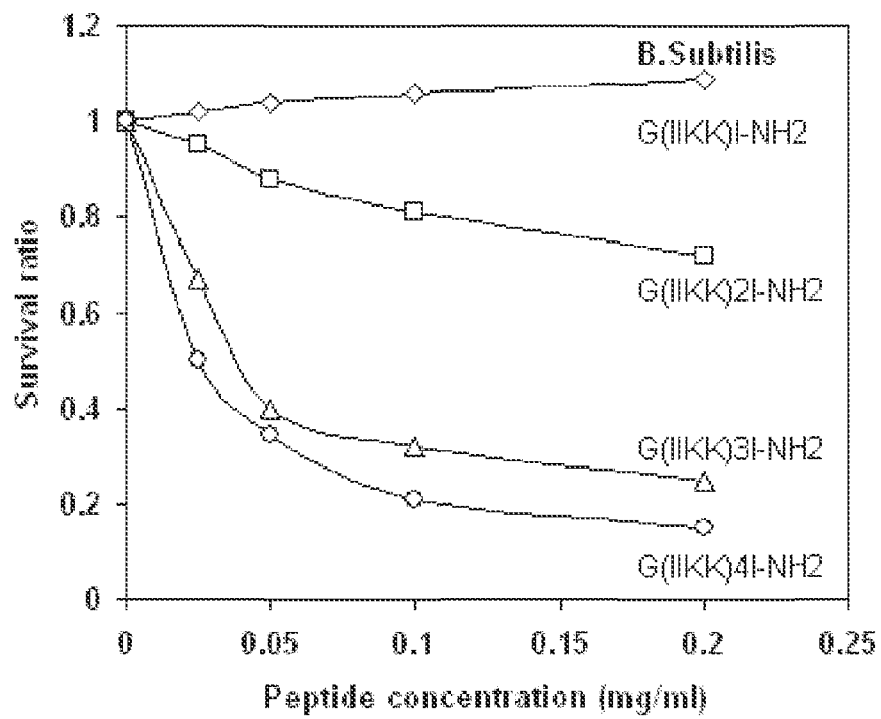
Figure 5A:
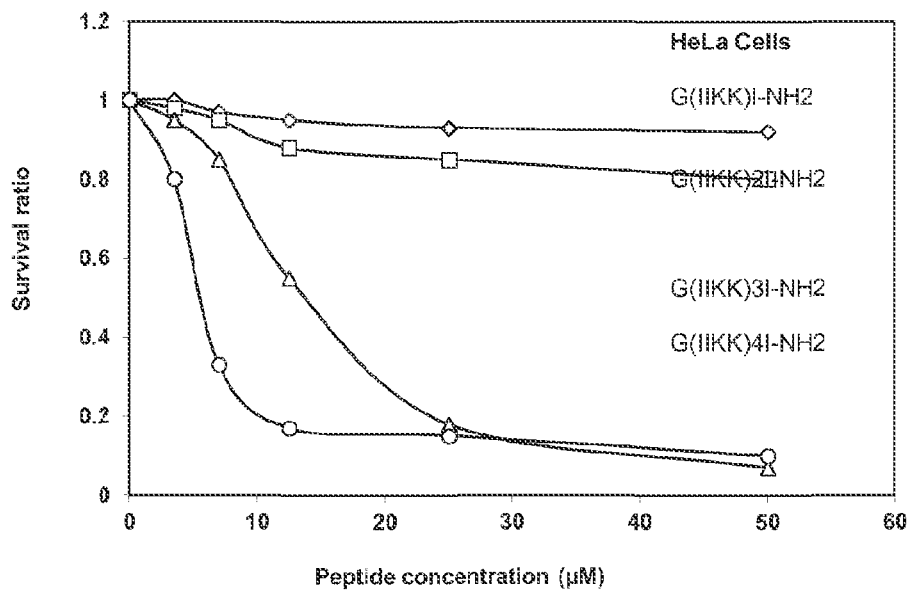
FIGS. 5A and 5B disclose SEQ ID NOS 1-4, respectively, in order of appearance.
Figure 5B:
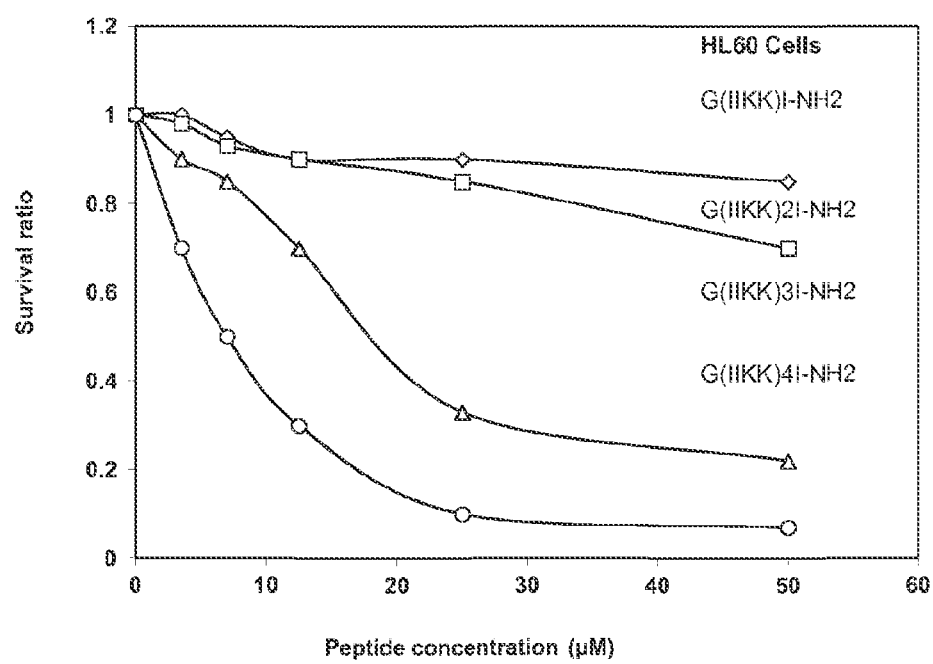
Figure 8:
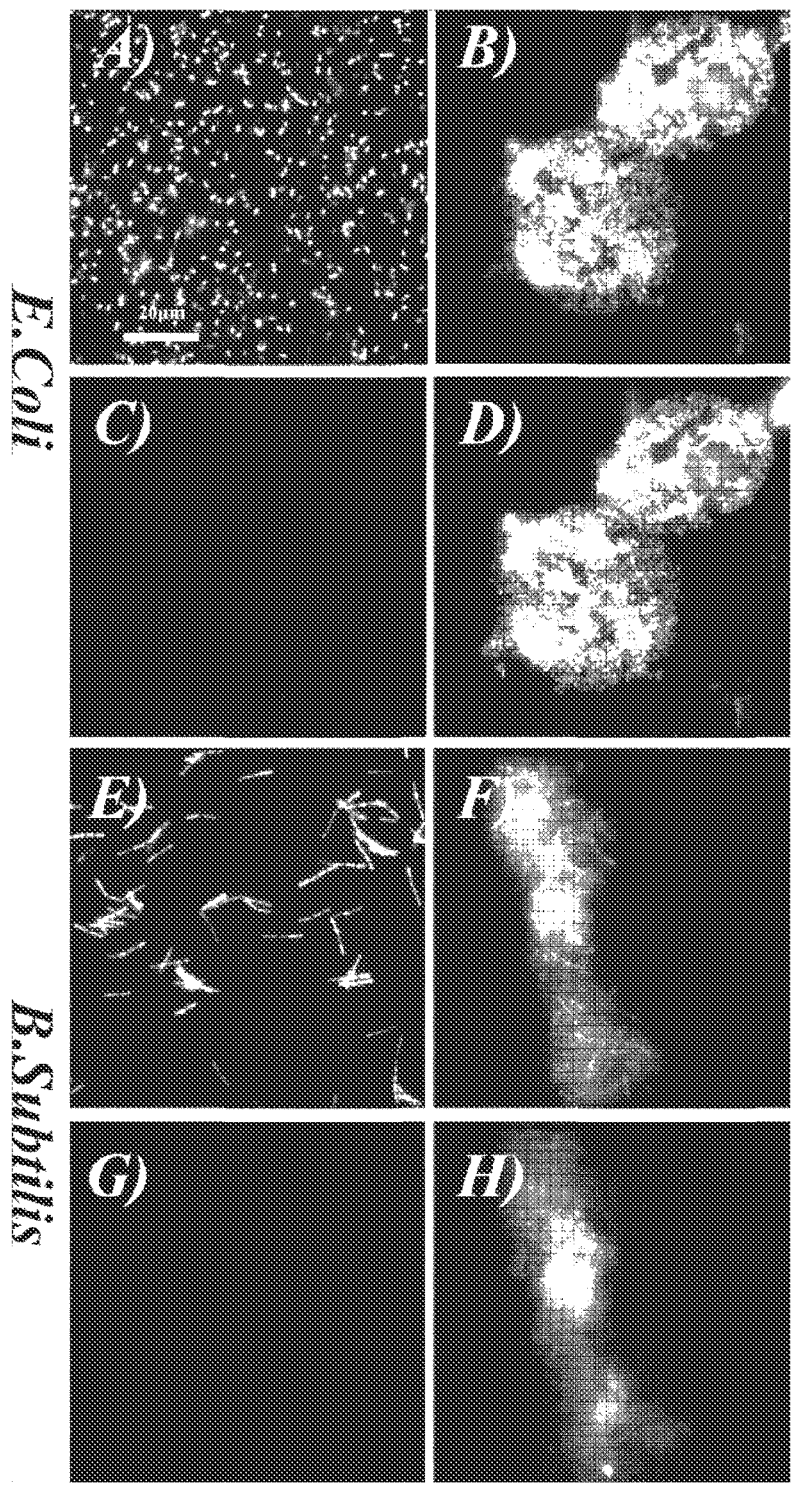
FIG. 8—Membrane lysis of *E. coli* DH5α (Panels A-D) and *B. subtilis* 168 (Panels E-H) in the presence of peptide 3 (G(IIKK)$_3$I-NH$_2$ (SEQ ID NO: 3)) at MIC (Panels B, D, F, H) or with control (Panels A, C, E, G), as observed by fluorescence microscopy. Panels A, B, E and F are obtained using DAPI dye. Panels C, D, G, H are obtained using FITC dye.
Figure 9:
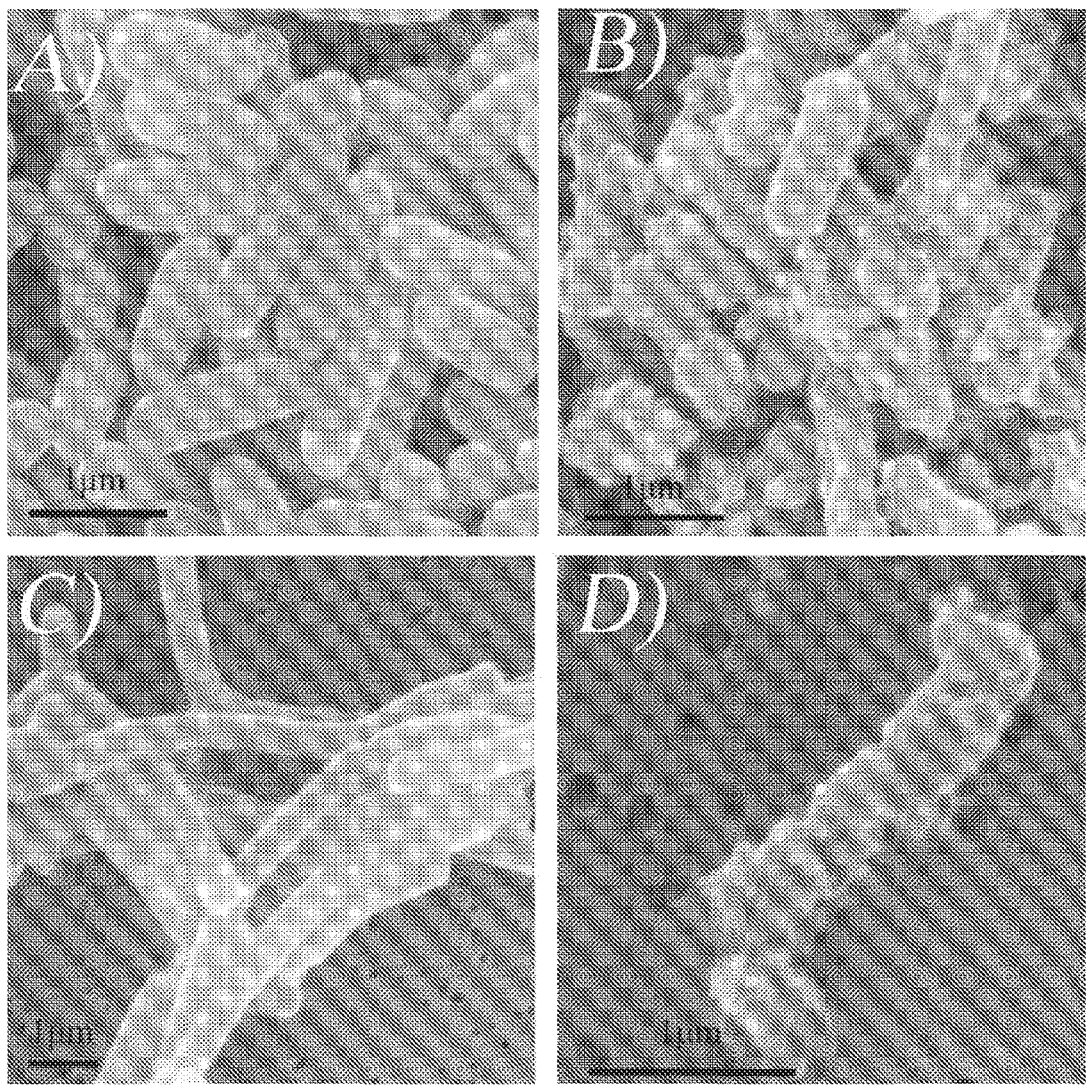
FIG. 9—Membrane lysis of *E. coli* DH5α (Panels A-B) and *B. subtilis* 168 (Panels C-D) in the presence of peptide 3 (G(IIKK)$_3$I-NH$_2$ (SEQ ID NO: 3)) at MIC (Panels B, D) or with control (Panels A, C), as observed by scanning electron microscopy (SEM).
Figure 10:
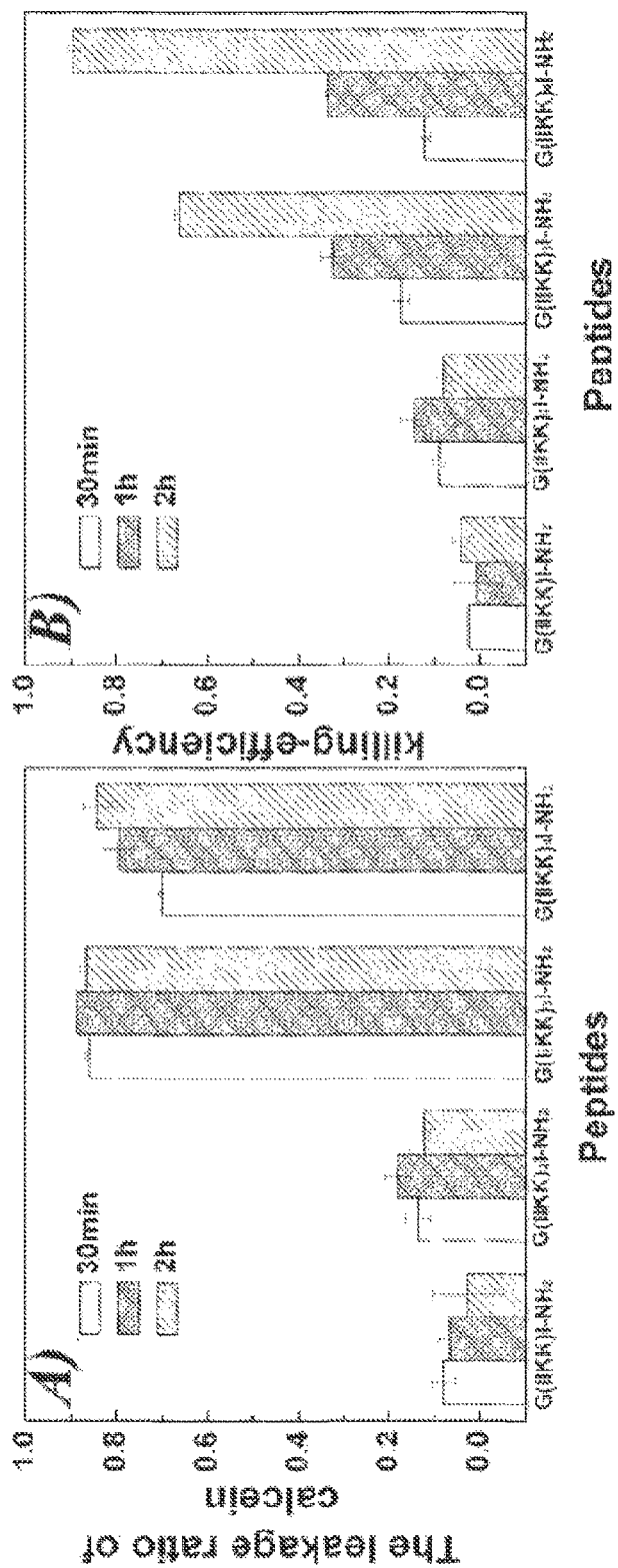
FIG. 10—(A) Leakage of calcein from HeLa cells in the presence of 0.1 mM of each of peptides 1-4, incubated for 30 min, 1 h and 2 h. (B) Cell viability of HeLa cells under similar conditions as for (A) and assessed using MTT assays.
Figure 11:
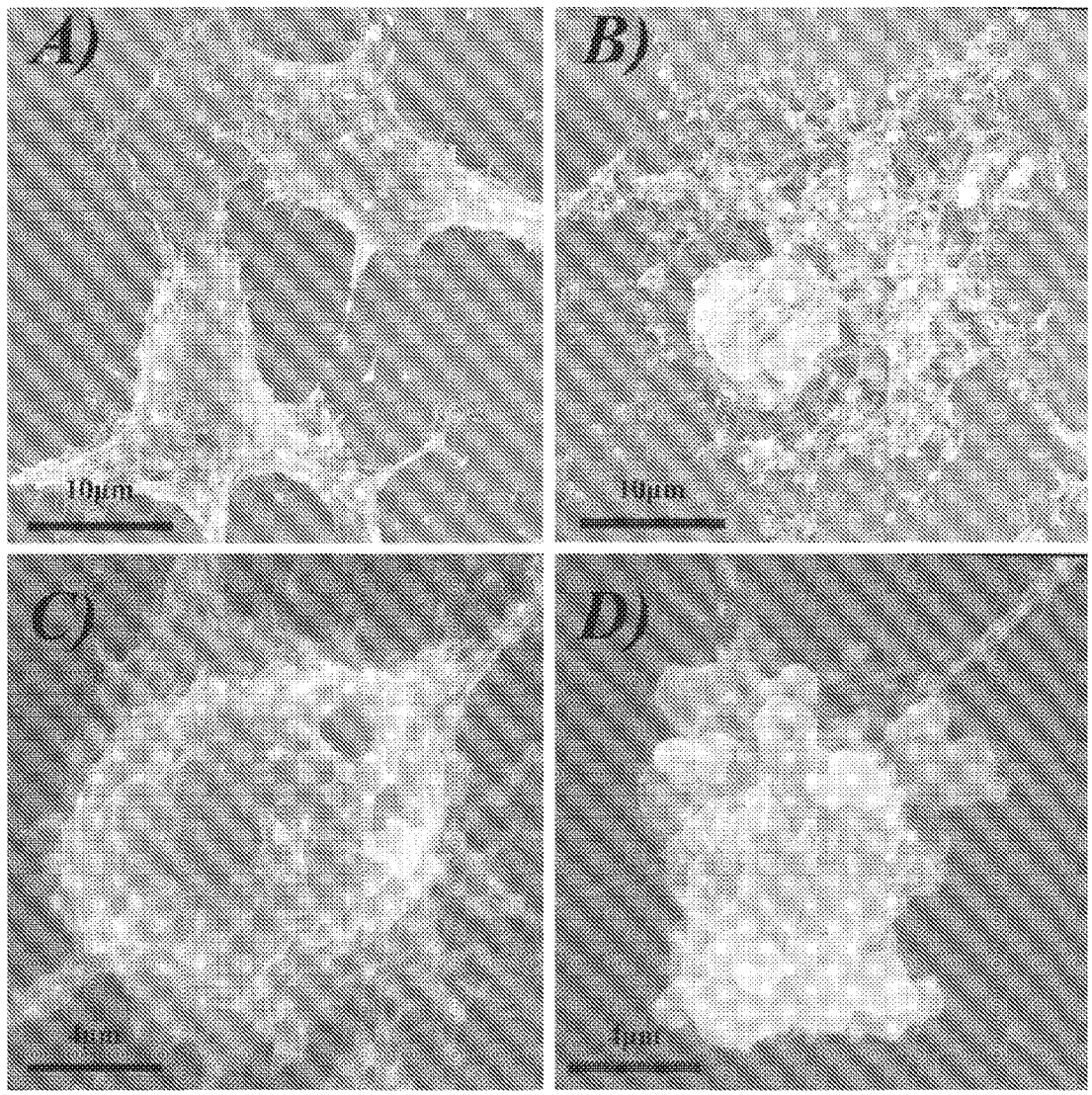
FIG. 11—Evidence of membrane damage and cell breakdown in HeLa cells incubated under 10 μM peptide 3 (G(IIKK)$_3$I-NH$_2$ (SEQ ID NO: 3)) for 24 h, and as observed using SEM imaging. (A) Normal cells. (B) Membrane breakdown. (C) Local membrane damage. (D) Apoptosis.

The inventors further found that the (IIKK (SEQ ID NO: 24)) containing peptides, and other similar peptides (peptides 5-9 in the present Examples) have antibacterial activity against *E. coli* and *B. subtilis* (Example 2; FIGS. 4 and 7), and have examined the mechanism of this activity to show that the peptides act by disruption of the cell membranes (Example 5; FIGS. 8 and 9). The inventors further showed that the peptides have antitumor activity against HeLa and HL60 cancer cell lines (Example 3; FIGS. 5 and 7), and have examined the mechanism of this activity to show that the peptides act by disruption of the cell membranes (Example 6; FIGS. 10 and 11).

Figure 6:
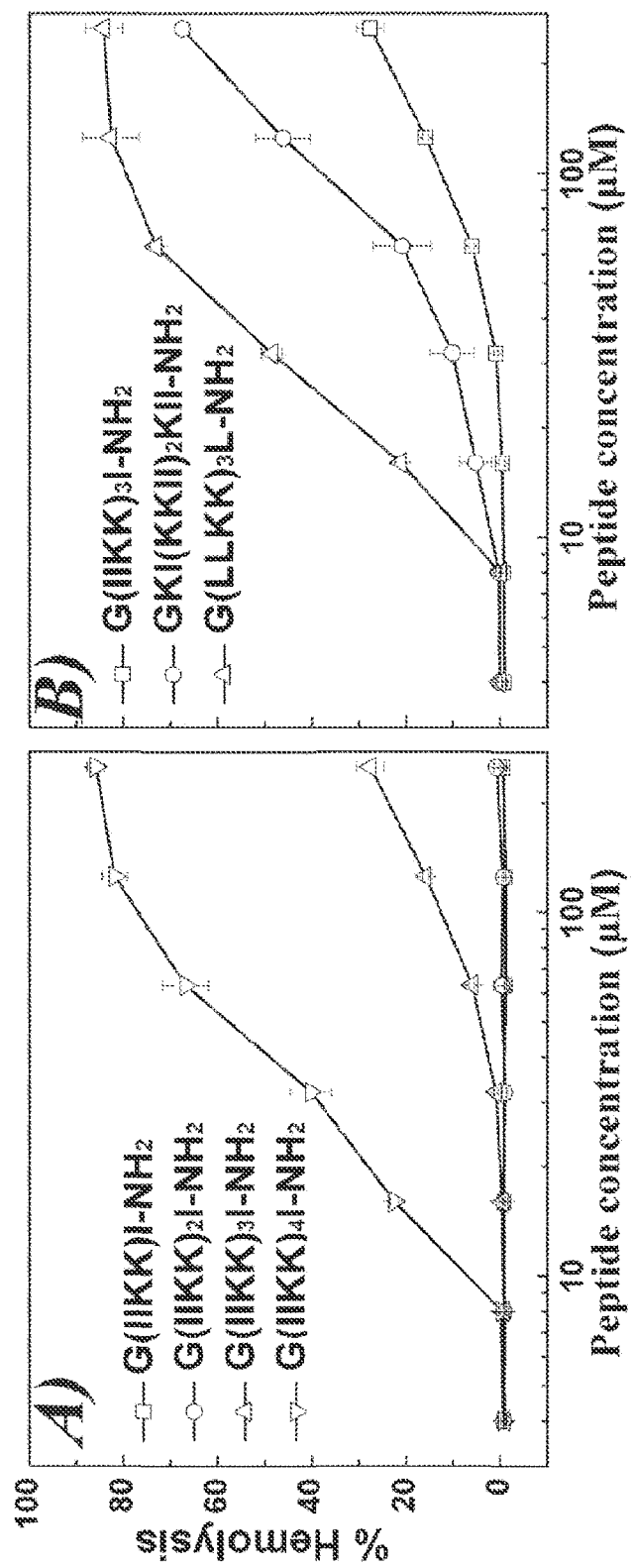
FIG. 6—The hemolytic activities of peptides 1-4 (G(IIKK)$_n$I-NH$_2$ (n=1-4) (SEQ ID NO: 23) series) (A) and of peptides 3, 5 and 8 (G(IIKK)$_3$I-NH$_2$ (SEQ ID NO: 3), G(LLKK)$_3$L-NH$_2$ (SEQ ID NO: 5), and GKI(KKII)$_2$KII-NH$_2$ (SEQ ID NO: 8)) (B), in human red blood cells. Human red blood cells (hRBCs) were incubated in PBS with different concentrations of peptides for 1 h at 37° C., followed by the monitoring of hemoglobin release at 540 nm.
Figure 12:
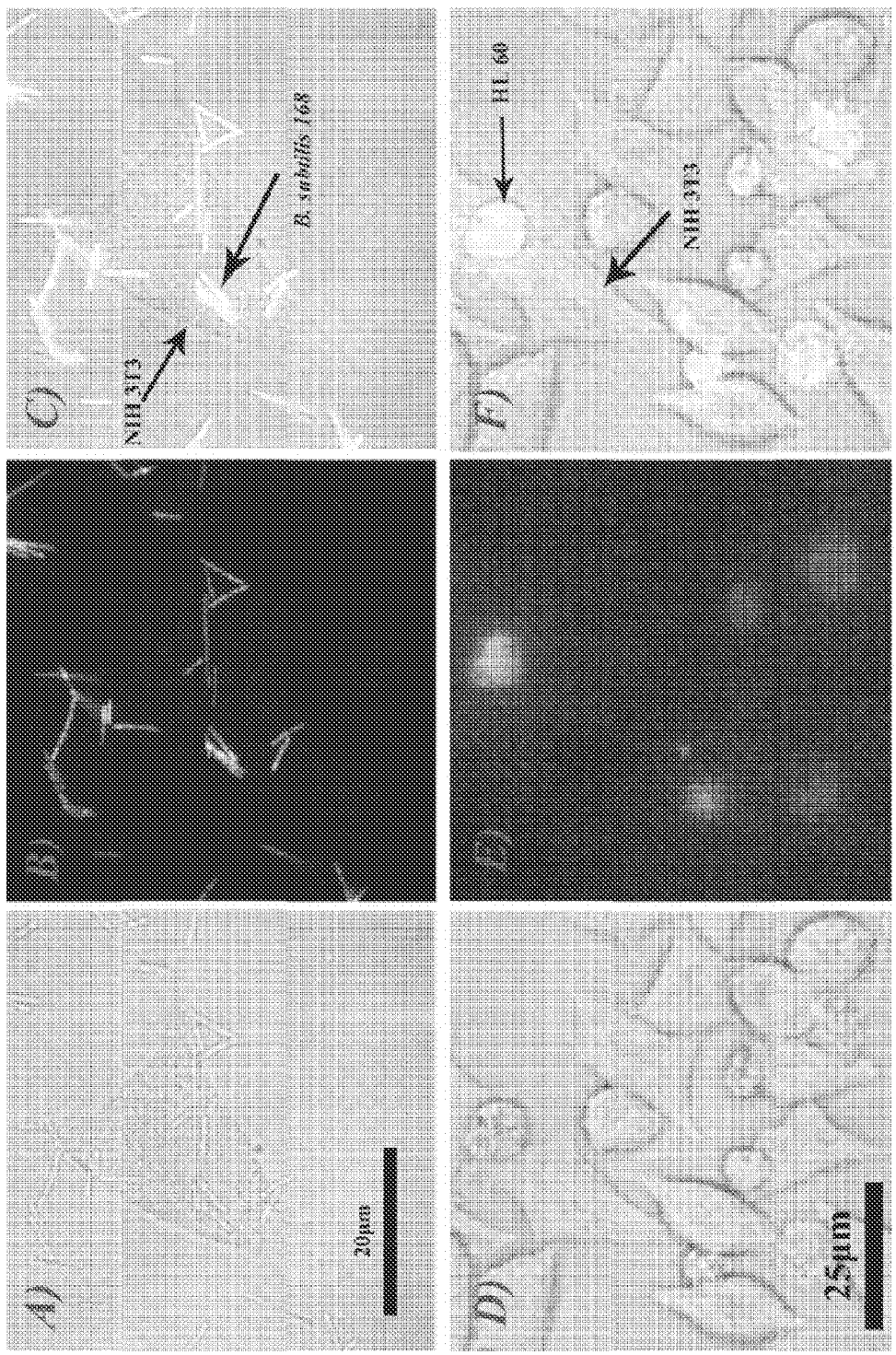
FIG. 12—Fluorescent images of the distribution of FITC-labeled peptide 3 (G(IIKK)$_3$I-NH$_2$ (SEQ ID NO: 3)) in two co-culture systems containing NIH 3T3 cells (model mammalian host) with bacteria *B. subtilis* 168 (upper panel) or HL60 cancer cells (bottom panel). (A) and (D) are the images observed under the bright field; (B) and (E) are the images acquired under blue exciting light; (C) and (F) are the overlapping images of (A) and (B), and (D) and (E), respectively. In these images, adherent cells are NIH 3T3, rod-like cells are *B. subtilis* 168 and round suspension cells are HL 60 as marked by black arrows.

For therapeutic use, it is important that a peptide which targets the cell membrane of bacteria or cancer cells, does not cause substantial damage to normal host cells. The inventors examined the hemolytic activity of the present peptides in human red blood cells, and showed that, the EC50 value (peptide concentration required to induce 50% lysis of the blood cells) was much higher than either the MIC value (lowest peptide concentration to inhibit bacterial growth) for *E. coli* or *B. subtilis*, or the IC50 value (peptide concentration causing 50% tumor cell growth inhibition) in HeLa or HL60 cells (Example 4; FIGS. 6 and 7). The inventors further confirmed selectivity for bacterial/cancer cells compared to normal host cells, by coculturing normal mammalian host cells (NIH 3T3 cells) with *B. subtilis* bacterial cells or with HL60 cancer cells, in the presence of peptide 3 (G(IIKK)$_3$I-NH$_2$ (SEQ ID NO: 3)). The peptide selectively targeted the bacterial and cancer cells, but did not bind or associate with the normal host cells (Example 7; FIG. 12). To the best knowledge of the inventors, this is the first in vitro selectivity assay ever reported for such studies.

Accordingly, in a first aspect, the invention provides a peptide of formula I or II shown below

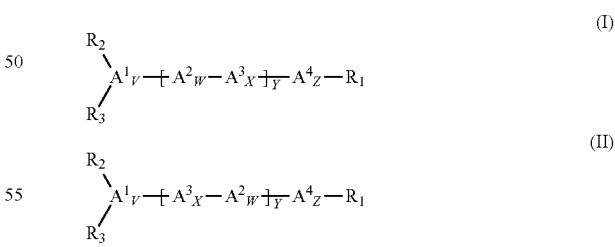

wherein:
A$^1$ is absent or an amino acid;
v is an integer selected from 0, 1, 2 or 3;
A$^2$ is, independently for each occurrence, a hydrophobic amino acid;
w is an integer selected from 2 to 10;
A$^3$ is a hydrophilic amino acid;
x is an integer selected from 1 to 5;
y is 1, 2, 3 or 4;

A⁴ is absent or an amino acid;

z is 0, 1, 2 or 3;

$R_1$ is a terminal substituent selected from OH, $NH_2$, (1-18C) alkyl, $N[(1-18C)alkyl]_2$ or NH(1-18C)alkyl;

$R_2$ and $R_3$ are both independently selected from H, (1-18C) alkyl or (2-18C)acyl;

or a salt thereof.

In the first aspect, $A^2$ may be any suitable hydrophobic amino acid, either naturally occurring or synthetic. In certain aspects, it is preferred that $A^2$ is a naturally occurring amino acid, and/or that the $A^2$ unit comprises only naturally occurring amino acids.

A hydrophobic amino acid in general refers to an amino acid having a hydrophobic side chain including alanine (A), isoleucine (I), leucine (L), valine (V), phenylalanine (F), tryptophan (W), tyrosine (Y), and glycine (G) and those amino acids that are more hydrophobic than charged and polar amino acids, including methionine, cysteine and proline. In one aspect, $A^2$ may be selected from A, V, I, L, M, P, F, Y and W. In another particular aspect, $A^2$ is V or I.

$A^2$ may also be a synthetic hydrophobic amino acid, for example, a synthetic analog of any of the above mentioned naturally occurring hydrophobic amino acids.

Suitably, $A^2$ is selected from I, L, V, F, Y and W. Suitably, $A^2$ is selected from I, L and V, such as I or V. Most suitably, $A^2$ is I.

$A^3$ may be any suitable hydrophilic amino acid, either naturally occurring or synthetic. In an embodiment, $A^3$ is a naturally occurring amino acid, and/or that the $A^3_x$ unit comprises only naturally occurring amino acids.

A hydrophilic amino acid in general refers to an amino acid having charge or a polar group on a side chain. Such amino acids include for example: amino acids with positively charged (cationic) side chains such as histidine (H), lysine (K) and arginine (R); amino acids with negatively charged side chains such as aspartic acid (D), glutamic acid (E); amino acids with polar uncharged side chains such as serine (S), threonine (T), asparagine (N) and glutamine (Q). On a relative basis, some weakly hydrophobic amino acids can be regarded as relatively hydrophilic, depending on their relative ranking in a given peptide sequence. For example, glycine (G) can be regarded as relatively hydrophilic in some instances.

$A^3$ may be a synthetic hydrophilic amino acid, for example, a synthetic analog of any of the above mentioned naturally occurring hydrophilic amino acids. Suitable synthetic amino acids include those in which the side chain comprises $(CH_2)_n$—$NH_2$ where n=1, 2, 3, or 4, or those amino acids in which the side chain comprises $(CH_2)_n$—COOH, where n=1, 2, 3 or 4. For example, $A^3$ may be a cationic amino acid such as ornithine (O), Dap or Dab as described herein.

Suitably, $A^3$ is a cationic amino acid, such as selected from H, K, and R or a synthetic analog thereof such as ornithine, Dap or Dab. Most suitably, $A^3$ is K or O, such as K. In a second aspect, the invention provides a peptide of formula I or II shown above wherein:

$A^1$ is absent or an amino acid;

v is an integer selected from 0, 1, 2 or 3;

$A^2$ is, independently for each occurrence, a hydrophobic amino acid selected from isoleucine (I) or valine (V);

w is an integer selected from 2 to 10;

$A^3$ is a hydrophilic amino acid selected from lysine (K) or ornithine (O);

x is an integer selected from 1 to 5;

y is 2, 3 or 4;

$A^4$ is absent or an amino acid;

z is 0, 1, 2 or 3;

$R_1$ is a terminal substituent selected from OH, $NH_2$, (1-18C) alkyl, $N[(1-18C)alkyl]_2$ or NH(1-18C)alkyl;

$R_2$ and $R_3$ are both independently selected from H, (1-18C) alkyl or (2-18C)acyl;

or a salt thereof.

In an embodiment of the first and second aspects, v is ≥1. In a particular embodiment of the first and second aspects, v=1.

In an embodiment of the first and second aspects, the unit defined by $A^1_v$ blocks the left-hand end of the peptide and improves stability of the peptide. In one embodiment of the first and second aspects, aspect $A^1$ is an amino acid. In a particular embodiment of the first and second aspects, $A^1$ is an amino acid selected from glycine (G), lysine (K) and isoleucine (I). In a particular embodiment of the first and second aspects, the $A^1_v$ unit is selected from G, GKI, or GIK. In a preferred embodiment of the first and second aspects, the $A^1_v$ unit is G.

In an embodiment of the first and second aspects, z is ≥1. In a particular embodiment of the first and second aspects, z is 1.

In an embodiment of the first and second aspects, the unit defined by $A^4_z$ improves stability of the peptide. In a particular embodiment of the first and second aspects, $A^4$ is an amino acid. In another embodiment of the first and second aspects, $A^4$ is an amino acid selected from isoleucine (I), leucine (L), valine (V) and lysine (K). Suitably, the $A^4_z$ unit is selected from I, L, V and KII. Most suitably, the $A^4_z$ unit is I. In an embodiment of the first and second aspects, the $A^4_z$ unit, or $A^4$ in the peptide comprises the same amino acid(s) as $A^2_w$ or $A^2$.

The groups $A^1$ and/or $A^4$ may be selected to alter or disrupt a hydrophilic and/or hydrophobic surface of the peptide upon adopting a helical structure. This can be assessed by drawing a helical circle or wheel representing the peptide, as described herein. Alteration or disruption of such a surface can affect the strength or propensity of the alpha-helical structure of the peptide, which can affect interaction of the peptide with cell surfaces, and so cell selectivity. Thus, cell selectivity can be tuned by selection of $A^1$ and/or $A^4$.

In an embodiment of the second aspect of the invention, $A^2$ is I.

In the first or second aspects, $A^2$ is, for each occurrence, independently selected.

In a particular embodiment of the first and second aspects, in the $A^2_w$ unit, $A^2$ is the same amino acid for all occurrences. For example, the $A^2_w$ unit may comprise II, LL or VV. Suitably, the $A^2_w$ unit is II.

In an embodiment of the first and second aspects, w may be an integer selected from 2 to 7, or from 2 to 5, such as 2, 3, 4, or 5. In a particular embodiment, w is 2.

In another embodiment of the second aspect, $A^3$ is K.

In an embodiment of the first and second aspects, x may be an integer selected from 1 to 3, or from 1 to 2. In a particular embodiment, x is 2.

In one embodiment of the first and second aspects, when x>1, each occurrence of $A^3$ is independently selected. In one preferred embodiment of the first aspect, when x>1, the $A^3_x$ unit comprises at least one cationic amino acid. The unit may comprise additional anionic or non-charged hydrophilic amino acids such as those described above, provided that the unit retains an overall positive charge. These non-cationic amino acids may provide spaced cationic patches and weaken cationic charge distribution on a helical wheel representing the peptide. In one embodiment, when x>1, each occurrence of $A^3$ in the $A^3_x$ unit is a cationic amino acid as described herein.

In a particular embodiment of the first and second aspects, in the $A^3_x$ unit, when x>1, $A^3$ is the same amino acid for all occurrences, e.g. the same cationic amino acid. For example, the $A^3_x$ unit may comprise HH, KK or RR or OO. Suitably, the unit comprises KK or OO, particularly KK.

In an embodiment of the first and second aspects, the ratio of hydrophobic to hydrophilic, e.g. cationic, amino acids in the $[A^2_w\text{-}A^3_x]$ unit or in the $[A^3_x\text{-}A^2_w]$ unit is 1:1. In an embodiment, x=w in the peptide. In one preferred embodiment, x=w=2.

In a particular embodiment of the first aspect, in the $[A^2_w\text{-}A^3_x]$ unit or in the $[A^3_x\text{-}A^2_w]$ unit, $A^2_w$ is selected from II, LL and VV, and $A^3_x$ is selected from HH, KK, RR and OO. Thus, for example, the $[A^2_w\text{-}A^3_x]$ unit may be selected from IIHH (SEQ ID NO: 25), IIKK (SEQ ID NO: 24), IIRR (SEQ ID NO: 26), IIOO (SEQ ID NO: 27), LLHH (SEQ ID NO: 28), LLKK (SEQ ID NO: 29), LLRR (SEQ ID NO: 30), LLOO (SEQ ID NO: 31), VVHH (SEQ ID NO: 32), VVKK (SEQ ID NO: 33), VVRR (SEQ ID NO: 34) and VVOO (SEQ ID NO: 35), and the $[A^3_x\text{-}A^2_w]$ unit may be selected from HHII (SEQ ID NO: 36), HHLL (SEQ ID NO: 37), HHVV (SEQ ID NO: 38), KKII (SEQ ID NO: 39), KKLL (SEQ ID NO: 40), KKVV (SEQ ID NO: 41), RRII (SEQ ID NO: 42), RRLL (SEQ ID NO: 43), RRVV (SEQ ID NO: 44), OOII (SEQ ID NO: 45), OOLL (SEQ ID NO: 46) and OOVV (SEQ ID NO: 47).

In a particular embodiment of the second aspect, in the $[A^2_w\text{-}A^3_x]$ unit or in the $[A^3_x\text{-}A^2_w]$ unit, $A^2_w$ is selected from II or VV, and $A^3_x$ is selected from KK and OO. Thus, for example, the $[A^2_w\text{-}A^3_x]$ unit may be selected from IIKK (SEQ ID NO: 24), IIOO (SEQ ID NO: 27), VVKK (SEQ ID NO: 33) and VVOO (SEQ ID NO: 35), and the $[A^3_x\text{-}A^2_w]$ unit may be selected from KKII (SEQ ID NO: 39), KKVV (SEQ ID NO: 41), OOII (HQ ID NO: 45), and OOVV (SEQ ID NO: 47).

In a preferred embodiment of the first aspect, $A^2_w$ is selected from II, LL and VV, and $A^3_x$ is selected from KK, and OO. Examples include those in peptides 1-9 described herein: IIKK (SEQ ID NO: 24), LLKK (SEQ ID NO: 29), VVKK (SEQ ID NO: 33), IIOO (HQ ID NO: 27), and KKII (SEQ ID NO: 39). Preferred $[A^2_w\text{-}A^3_x]$ or $[A^3_x\text{-}A^2_w]$ units include those where $A^2_w$ is II and $A^3_x$ is KK or OO. A preferred unit is IIKK (SEQ ID NO: 24), KKII (SEQ ID NO: 39), or IIOO (SEQ ID NO: 27).

In a preferred embodiment of the second aspect, $A^2_w$ is selected from II and VV, and $A^3_x$ is selected from KK and OO. Examples include those in peptides 1-9 described herein: IIKK (SEQ ID NO: 24), VVKK (SEQ ID NO: 33), IIOO (HQ ID NO: 27), and KKII (SEQ ID NO: 39). Preferred $[A^2_w\text{-}A^3_x]$ or $[A^3_x\text{-}A^2_w]$ units include those where $A^2_w$ is II and $A^3_x$ is KK or OO. A preferred unit is IIKK (SEQ ID NO: 24), KKII (SEQ ID NO: 39), or IIOO (SEQ ID NO: 27).

In one embodiment of the first and second aspects, the peptide is of formula I (comprising the $[A^2_w\text{-}A^3_x]$ unit).

In the first aspect, y may be selected from 1, 2, 3 or 4. In one embodiment, y is >1, such as 2, 3, or 4. In one particular embodiment, y is 3.

In the second aspect, y may be selected from 2, 3, or 4. In one embodiment, y is 2 or 3. In one particular embodiment, y is 3.

In a particular embodiment of the first and second aspects, $R_1$ is selected from $NH_2$, (1-10C)alkyl, NH(1-14C)alkyl or N([1-10C)alkyl]$_2$. For example, $R_1$ may suitably be $NH_2$. In a particular embodiment, $R_2$ and $R_3$ are independently selected from H (hydrogen), (1-10C)alkyl, and (2-10C)acyl, such as H, (2-10C)alkyl or (2-10C) acyl.

In one embodiment of the first and second aspects, when v≥1, $R_2$ and $R_3$ are both H (hydrogen).

In one embodiment of the first and second aspects, in a peptide of the invention:
$A^1$ is G and v=1;
$A^2_w$ is II or VV, preferably II;
$A^3_x$ is KK or OO, preferably KK;
$A^4$ is I and z=1; and
y=2-4, preferably 3.

In one preferred embodiment in the peptide $R_1$ is $NH_2$, and both $R_2$ and $R_3$ are H.

Examples of peptides according to the invention include peptides 1-9 described herein in the present Examples, and listed in Table 1. Particularly preferred are: peptide 2 (G(IIKK)$_2$I-NH$_2$ (SEQ ID NO: 2)); peptide 3 (G(IIKK)$_3$I-NH$_2$ (SEQ ID NO: 3)); peptide 4 (G(IIKK)$_4$I-NH$_2$ (SEQ ID NO: 4)); and peptide 7 (G(IIOO)$_3$I-NH$_2$ (SEQ ID NO: 7)). Particularly preferred peptides are peptides 3 and 7, such as peptide 3.

A peptide according to the invention is typically both cationic and amphiphilic. By cationic is meant that the peptide bears an overall positive charge. In general this refers to the peptide charge at a given pH, e.g. below pH 10, or the pKa of any cationic amino acid(s) in the peptide. In one aspect, the charge is as at physiological pH, e.g. pH 7 or 7.4. For example, a peptide may comprise positive charge, such as 2, 3, 4, 5, 6, 7, 8, 9, or more positive charges. By amphiphilic is meant that the peptide comprises both hydrophilic and hydrophobic (lipophilic) properties. In general such a peptide has both a polar, water-soluble group and a non-polar, water-insoluble group, e.g. a hydrocarbon chain.

In one aspect, peptides herein typically adopt or are capable of adopting α-helical structure e.g. on interaction with negatively charged lipid. These peptides typically can be represented in a Schiffer-Edmundson wheel projection. Such a projection typically has a predominantly hydrophobic and a predominantly hydrophilic surface.

In one aspect, a peptide of the invention may comprise less than or equal to 20 amino acids, such as less than or equal to 19, 18, 17, 16, 15 or 14 amino acids. A peptide may comprise, for example, 4, 5, 6, 7, 8, 9, 10, 11, 12 or 13 amino acids.

In one aspect a peptide comprises naturally occurring amino acids only. Such a peptide may be considered to be a natural peptide. Natural peptides may be preferred for particular applications.

A suitable salt of a compound of formula I or II is a pharmaceutically acceptable salt. Such salts may be, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Preparation of Peptides

Peptides may be synthesised and purified by any suitable means. For example, solid-phase peptide synthesis on Rink amide MBHA resin may be used, as in the present Examples.

Alternatively, nucleic acids encoding the peptides may be prepared by routine methods and expressed to form the peptides. In one aspect the present invention relates to a nucleic acid encoding a peptide of the invention, and to the use of the nucleic acid in preparing the peptide.

Functional Properties of the Peptides of Formula I and II

The peptides of the present invention have surfactant properties. Thus, the peptides are capable of reducing surface tension of a liquid such as water.

The peptides of the present invention may possess antibacterial activity. By this is meant that a peptide is able to inhibit bacterial growth to a given extent as determined in a suitable assay. Activity may be shown against gram positive bacteria (such as *B. subtilis* or *S. aureus*), and/or gram negative bacteria (such as *E. coli*). In one aspect, activity against gram positive bacteria may be higher than activity against gram negative bacteria. Without wishing to be bound by any particular theory, it is believed that the peptide interacts with and damages the bacterial cell membrane.

Typically, antibacterial activity may be expressed in terms of an MIC value (minimal inhibitory concentration: the lowest peptide/drug concentration to inhibit bacterial growth). Preferably a peptide has an MIC value of 1-130 µM, for example, 1-120, 1-110, 1-100, 1-90, 1-80, 1-70, 1-60, 1-50, 1-40, 1-30, 1-20 µM and more preferably 1-10 µM against *E. coli*, e.g. as determined using an assay described herein. Preferably a peptide has an MIC value of 0.5-100 µM, for example, 0.5-90, 0.5-80, 0.5-70, 0.5-60, 0.5-50, 0.5-40, 0.5-30, 0.5-20 µM and more preferably 0.5-10 µM against *B. subtilis*, e.g. as determined using an assay described herein. Suitably a peptide has an MIC value less than or equal to that determined when using peptides such as G(IIKK)$_3$I-NH$_2$ (SEQ ID NO: 3) and G(IIOO)$_3$I-NH$_2$ (SEQ ID NO: 7) described herein. Suitably a peptide has an MIC value less than or equal to that of a known antibiotic such as any of those described herein (see FIG. 7).

Antibacterial activity of a peptide may be assayed and examined by any suitable means, including those described herein in the Examples. Thus, for example, an assay to determine MIC value may comprise:

adding aliquots (e.g. 100 µl) of bacterial suspension of known concentration (colony-forming units (CFU)/ml) to a given volume (e.g. 100 µl) of peptide solution in each well of a multiwell plate, where peptide solutions are provided as a dilution series (e.g. 2-fold serial dilutions in 10 mM PBS buffer);

incubating for a suitable time and temperature to allow bacterial growth in the absence of peptide (e.g. 18-24 h at 37° C.);

assessing bacterial growth by any suitable means (e.g. measuring the absorbance at 600 nm with a microplate ELISA reader.); and defining MIC as the lowest concentration of peptide for which there is no visible growth.

Suitably, a peptide demonstrates antibacterial activity as within the limits of detection of the assay used.

Typically for a peptide of Formula I or II having antibacterial activity, y in Formula I or II is >1, for example y=2, 3 or 4.

A peptide of the invention may also have antitumor activity. By this is typically meant that a peptide is able to reduce cancer cell viability (or inhibit cancer cell growth to a given extent) as determined in a suitable assay.

A peptide may be active against any suitable cancer cell or cell line, for example HeLa and/or HL60 cells. Antitumor activity may be expressed in terms of an IC50 value (peptide concentration causing 50% tumor cell growth inhibition). Preferably a peptide has an IC50 value which is less than or equal to that determined for peptide G(IIKK)$_3$I-NH$_2$ (SEQ ID NO: 3) or peptide G(IIOO)$_3$I-NH$_2$ (SEQ ID NO: 7) in an assay such as those described herein (see Table 3, FIG. 7). In one aspect, a peptide may have an IC50 value of 1-70 µM for HeLa cells, for example 1-60, 1-50, 1-40, 1-30, 1-25, 1-20, or 1-10 µM. In one aspect, a peptide may have an IC50 value for HL60 cells of 1-100 µM, for example, 1-90, 1-80, 1-70, 1-60, 1-50, 1-40, 1-30, 1-20 or 1-10 µM such as 5-25 µM.

Antitumor activity of a peptide may be assayed and examined by any suitable means, including those described herein in the Examples. For example, an 3-(4,5-dimethyl-thiazol-2-yl)-2,5-diphenyl tetrazolium bromide (MTT) cell viability assay may be used, and the IC$_{50}$ value calculated as the concentration of peptide that induced 50% growth inhibition compared to the untreated control. MTT is a yellow compound which is reduced to purple formazan in the mitochondria of living cells. Reduction requires active mitochondrial enzymes, and can therefore act as an indicator of viable cells.

Thus, for example, an assay to determine IC50 value may comprise: seeding cancer cells in suitable medium for a suitable time period (e.g. in a suitable multiwall plate at $10^5$ cells/well in a complete medium, such as Iscove's modified dulbecco's medium (IMDM), with 10% fetal bovine serum (FBS) for 24 h)

treating the cancer cells with a peptide dilution series (e.g. 2-fold diluted peptides, to give final concentrations of 50, 25, 12.5, 6, 25 and 3 µM)

incubating for a suitable time, e.g. 24 h adding a suitable amount of MTT (e.g. 20 µl of a 5 mg/ml solution per well) and incubating for a suitable time and temperature (e.g. 4 h at 37° C.);

removing supernatant and adding a suitable amount of dimethyl sulfoxide (DMSO), e.g. 150 µl per well, to dissolve formazan crystals; and measuring absorbance at 570 nm, e.g. using a microplate ELISA Reader.

Samples without cells for blanking the spectrophotometer and samples of cells without peptides may be taken as negative controls.

Suitably the peptide demonstrates antitumor activity within the limits of detection of the assay used.

Typically, for a peptide of Formula I or II having antitumor activity, y in Formula I or II is >1, for example y=2, 3 or 4.

Suitably a peptide of the invention selectively interacts with bacterial and/or tumor cells, and does not substantially interact with or damage normal host cells.

A host as used herein generally refers to an organism which has a bacterial infection and/or cancerous cells, and which is to be treated with a peptide of the invention. In general the host is a mammal, such as a human. A host may be an animal such as a domestic pet or farm animal, e.g. dogs, cats, rabbits, horses, chickens, pigs or sheep. By normal host cells is meant cells in or of the host organism which it is not desired to target with the peptide, or a cell line derived therefrom. This includes for example, host cells which are non-bacterial or non-cancerous, or a cell line derived therefrom. Normal host cells or cell lines may include, for example, human red blood cells, or NIH 3T3 cells or human dermal fibroblast cells.

Selectivity of a peptide for bacterial or cancerous cells, compared to normal host cells may be determined using any suitable assay or assays, including those used in the present Examples.

In one aspect, a peptide may show selective interaction with a lipid mimic of bacterial/tumor cell membranes (e.g. DPPG) compared to a lipid mimic of normal mammalian host cell membranes (e.g. DPPC). This can be assessed, for example, by determining change in lipid surface pressure in the presence of the peptide or by use of CD spectra to determine a change in secondary structure of the peptide, e.g. formation of an ordered helical structure, in the presence of the lipid mimic (e.g. lipid SUVs). Suitable methods are described in Example 1 herein. Preferably a peptide has stronger affinity and often produces a significantly greater increase in surface pressure in a lipid mimic of bacterial/tumor cell membranes (e.g. DPPG) than a lipid mimic of normal mammalian host cell membranes (e.g. DPPC). Preferably a peptide undergoes a change in secondary structure on incubation with SUVs of a lipid mimic of bacterial/tumor cell membranes (e.g. DPPG) but not or to a far lesser extent on incubation with SUVs of a lipid mimic of normal mammalian host cell membranes (e.g. DPPC).

In a preferred aspect, a peptide displays antibacterial activity and/or antitumor activity at a peptide concentration which produces no or substantially no reduction in viability of normal host cells.

The effect of a peptide on normal host cells may be determined using any suitable assay. One example is a hemolytic assay carried out in red blood cells, as in Example 4, which may be used to determine an EC50 value (the peptide concentration needed to induce 50% lysis of the blood cells in the assay). Thus, for example, an assay may comprise:

mixing an aliquot of a suspension of human red blood cells (hRBCs) (e.g. 100 µl of hRBCs suspended in PBS at 8% (v/v)) with an aliquot of each member of a dilution series of peptide (e.g. 2-fold diluted peptides), in a multiwell plate;

incubating for a suitable time and temperature (e.g. 1 h at 37° C.) and centrifuging (e.g. 1000 g for 5 min); and transferring aliquots (e.g. 100 µl) of the supernatant to new multiwell plates and monitoring hemoglobin release by measuring absorbance at 540 nm (e.g. with a microplate ELISA Reader).

As negative and positive controls, hRBCs in PBS and 0.1% Triton X-100 may be employed. The hemolysis percentage may be calculated as follows:

$$\% \text{ hemolysis} = [(Abs_{540\ nm\ with\ peptide} - Abs_{540\ nm\ in\ PBS}) / [(Abs_{540\ nm\ with\ 0.1\%\ Triton\ X-100} - Abs_{540\ nm\ in\ PBS}) \times 100$$

In one aspect is it preferred that a peptide which is for antibacterial use has an EC50 value which is significantly higher than the MIC value of the peptide in an antibacterial assay such as those described herein. Similarly it is preferred that a peptide which is for antitumor use has an EC50 value which is significantly higher than the IC50 value of the peptide in an antitumor assay such as those described herein. For example, an EC50 value for a peptide may be at least 10-fold higher, such as 20-fold higher or more than a corresponding MIC value. Similarly, an EC50 value for a peptide may be at least 5-fold, 6-fold, 7-fold, or at least 10-fold higher, such as 20-fold higher or more than the corresponding IC50 value. Selectivity of a peptide may be further determined by co-culturing different cells in the presence of the peptide. Typically target cells (e.g. bacterial and/or cancer cells, such as any of those described herein) are co-cultured with non-target cells (normal host cells, such as any of those described herein). The co-culture is incubated with detectably labelled peptide (e.g. peptide bearing a fluorescent label such as FITC). Distribution of peptide is then assessed by detection of the label (e.g. by microscopy such as fluorescence microscopy). Preferably the peptide is associated with or in the target cells, and is not associated with or in the non-target cells. Such co-culturing is described for peptide 3 in Example 7 herein.

Applications

Uses

Peptides of formula I or II have a variety of uses.

The peptides of the first or second aspects of the invention may be used as surfactants. Surfactants are routinely employed in a wide variety of products and processes, where it is desirable to reduce surface tension, including as cleaning, wetting, dispersing, emulsifying, foaming and antifoaming agents. For example, surfactants may find use in: cleaning compositions, such as detergents, fabric softeners; agrochemical formulations such as herbicides and insecticides; biocides (sanitisers); personal care compositions, such as shampoos, conditioners; chemical compositions such as emulsions, paints, adhesives, inks; or in pharmaceutical compositions.

Peptides of Formula I or II of the first or second aspects of the invention having antibacterial activity may be used as a preservative, to prevent decomposition or undesirable chemical change in a substance or composition due to bacterial growth. For example, preservatives may be added to food, pharmaceuticals, paints, biological samples or wood.

The peptides of the first or second aspects of the invention having antibacterial activity may be used as antibacterial agents, for therapeutic or non-therapeutic purposes. Non-therapeutic use of an antibacterial agent may include, for example, use in cleaning products, or personal care compositions. Non-therapeutic use may be in vitro. Therapeutic use of an antibacterial agent is described further herein.

Peptides of Formula I or II of the first or second aspects of the invention having antitumor activity may be used as anti-cancer agents. This is described further herein.

Accordingly, in one aspect, the invention provides the use of a peptide of Formula I or II as a surfactant. The invention further provides the use of a peptide of Formula I or II as a preservative. The invention further provides the use of a peptide of Formula I or II as an antibacterial agent. The invention further provides the use of a peptide of Formula I or II as an anticancer agent.

It is apparent that, in use, a peptide may perform more than one function. For example, a peptide used in a cleaning composition may act as both an antibacterial agent and a surfactant. Similarly, a peptide used in a pharmaceutical composition for treating cancer, may act as both a surfactant and an anti-tumor agent. Accordingly, the invention also provides use of a peptide of Formula I or II for one or more of the above purposes simultaneously.

It is also apparent that one or more peptides of Formula I or II may be used together in any given application.

Medical Methods

Peptides of formula I or II of the first or second aspects of the invention having antibacterial or anti-tumor activity additionally have therapeutic applications, in treating bacterial infection or cancer in a subject.

Accordingly, the invention provides a peptide of formula I or II of the first or second aspects of the invention, or a pharmaceutically acceptable salt thereof, for use in the treatment of infection.

The invention further provides a method of treating infection comprising administering a therapeutically effective amount of a peptide of Formula I or II of the first or second aspects of the invention, or a pharmaceutically acceptable salt thereof, to an individual in need of such treatment.

The invention further provides a peptide of formula I or II of the first or second aspects of the invention, or a pharmaceutically acceptable salt thereof, for use in the treatment of cancer.

The invention further provides a method of treating cancer comprising administering a therapeutically effective amount of a peptide of Formula I or II of the first or second aspects of the invention, or a pharmaceutically acceptable salt thereof, to an individual in need of such treatment.

A subject or individual to be treated according to the invention is typically a mammalian subject, such as a human. A subject may be an animal such as a domestic pet or farm animal described herein.

An infection to be treated according to the present methods is typically a bacterial infection. The infection is in general of a bacterium which is susceptible to the peptide as described herein. The infection may be associated with or caused by gram negative bacteria and/or gram positive bacteria.

Examples of human pathogenic bacteria infections can be viewed, for example, at http://en.wikipedia.org/wiki/Pathogenic_bacteria. Examples include: bacterial vaginosis, bacterial meningitis, bacterial pneumonia, urinary tract infections, bacterial gastroenteritis and bacterial skin infections.

Common bacterial infections occur on skin. Bacteria such as *Staphylococcus* or *Streptococcus* are part of the normal human flora and usually exist on the skin or in the nose without causing disease, but can potentially cause skin infections, pneumonia, meningitis and even overwhelming sepsis, depending on host health conditions and other related circumstances. Impetigo and Erysipelas are for example common bacterial skin infections primarily caused by *Staphylococcus aureus*, and sometimes by *Streptococcus pyogenes*. Cellulitis is a diffuse inflammation of connective tissue with inflammation of dermal and subcutaneous layers of the skin. Cellulitis can be caused by normal skin flora or by exogenous bacteria, and often occurs where the skin has previously been broken, for example, cracks in the skin, cuts, blisters, burns, insect bites, surgical wounds, intravenous drug injection or sites of intravenous catheter insertion. Skin on the face or lower legs is most commonly affected by this infection. Bacteria also often cause urinary tract infections (UTI) and the main causal agent is *E. Coli*.

In addition, bacterial gastroenteritis and related digestive system infections associated with intake of food and drink, are caused by pathogenic enteric bacteria that are generally distinguished from the usually harmless bacteria in the normal gut flora, though the distinction is often not very obvious. Again, *E. Coli* is very often the causal agent in this group of infective pathogenic bacteria.

Cancer which is to be treated by the invention may be any cancer type. Typically, the cancer cells which are targeted are cells which are susceptible to the treating peptide as described herein. The present peptides have shown activity against HeLa cells derived from cervical cancer and HL60 cells derived from human promyelocytic leukemia as described herein. Thus in one aspect the peptides may be used to treat cervical cancer or promyelocytic leukemia. Examples of cancers include, for example, epithelial ovarian malignancies, skin cancers, breast cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas. Other cancerous conditions include acute myeloid leukemia, acute promyelocytic leukemia, acute lymphoblastic leukemia, chronic myelogenous leukemia, chronic lymphoblastic leukemia, Hodgkins disease and Non-Hodgkin Lymphomas.

Administration routes and dosage levels for use in the present methods are described further below.

In one aspect, an antibacterial or anti-tumor peptide of the invention may be used in combination with one or more other active agents, to treat infection or cancer. This is described further below.

Combination Products and Methods

As above, a peptide of Formula I or II may be used in therapy in combination with one or more other drugs. For example, an antibacterial peptide may be used in combination with other antibacterial agents such as any of those described herein. An anti-tumor peptide may be used in combination with other anticancer therapies such as any of those described herein Similarly, a peptide of Formula I or II may be used non-therapeutically as an anti-bacterial agent in combination with one or more other agents, e.g. in an antibacterial or personal care composition. Examples of combinations are described herein.

The various active ingredients which are for combined use may be administered simultaneously, sequentially or separately. The drugs or agents may be supplied in the same composition, or in different compositions for combined use, e.g. in a kit form.

Therefore in one aspect the invention relates to products for combined use in treating or preventing bacterial infection, the products comprising an antibacterial peptide of Formula I or II and one or more other antibacterial agents for administration separately, sequentially or simultaneously. The invention further relates to products for combined use in treating or preventing cancer, the products comprising an antitumor peptide of Formula I or II and one or more other anticancer agents for administration separately, sequentially or simultaneously. The invention further provides products for combined non-therapeutic antibacterial use, the products comprising an antibacterial peptide of Formula I or II and one or more other agents for use separately, sequentially or simultaneously.

Thus the present antimicrobial peptides can be used alone in formulations as the sole or main antimicrobial agent, or in combination with other agents. Without wishing to be bound by theory, peptides are believed to kill bacteria by disrupting the bacterial membrane. This is a unique process, different to that of both well known and newly developed pharmaceutical antimicrobials such as penicillin, metronidazole, tinidazole, cephamandole, latamoxef, cefoperazone, cefmenoxime, and furazolidone. When combined with other such antimicrobials to treat bacterial infection the present peptides can provide synergistic effects and therefore reduced doses by providing different treatment mechanisms.

For general personal care, the needs for antimicrobial efficacy vary and the purposes are usually associated with protection and prevention. The higher efficacies needed in pharmaceutical use are not generally required, and peptides of lower antimicrobial efficacy may be used. Thus, in personal care compositions, peptides can be formulated together with other antimicrobials including natural ones such as lactic acid, citric acid, acetic acid, and their salts, either as ingredients, or as disinfectants. This list also extends to plant extracts and plant oils including cinnamon oil, clove oil, eucalyptus oil, garlic, oregano oil, lavender oil, leleshwa oil, lemon oil, mint oil, neem oil, nigella sativa, peppermint oil, sandalwood oil, sideritis, tea oil, thyme oil, having varying antimicrobial activities. Plant derived phenols and terpenes are widely used as preservatives for food and are attractive as antimicrobials for personal care products. Their combined uses with peptide in formulated products offer benefits in synergy and efficacy.

Synthetic active antimicrobials used widely in personal care and general surface cleaning are mainly chlorhexidine gluconate (cationic), iodine and iodophors (requiring stabilization with a polymer and ethoxylated nonionic surfactants to reduce irritation from the iodine), quaternary ammonium compounds (most frequently used are alkyl benzalkonium chlorides and triclosan (nonionic, easy to be formulated with a variety of surfactants). Inactive or mild synergistic ingredients are water, cocaminopropyl betaine, propylene glycol, allantoin, cetrimonium chloride, quaternium 12, cocaminopropylamine oxide, diazolidinyl urea, quaternium 15, methyl paraben, propyl paraben, coloring agent, fragrance, TEA, citric acid.

In view of the known toxicity and side effects of such chemical antimicrobials, their reduced use or replacement by antimicrobial peptides such as those described herein has benefits to users and the environment.

Anticancer therapies which may be used in combination with the present peptides include any suitable cancer treatment, such as chemotherapy or radiotherapy. Anticancer drugs include, for example, cisplatin, referred to herein.

As described in the present Examples, the present peptides may be used in combination with one or more surfactants, particularly in products or compositions intended for application to skin or hair. A number of surfactants have been shown to enhance the antibacterial effect of the present peptides. The surface active egg membrane polypeptide Mx, for example, has been shown to enhance antibacterial activity of the peptides, e.g. the GO and G3 peptides (Example 12), despite an apparent lack of antibacterial activity for the Mx polypeptide when used alone. Accordingly in one aspect, the invention provides products for combined use in treating or preventing bacterial infection, the products comprising an antibacterial peptide of Formula I or II and one or more surfactants for administration separately, sequentially or simultaneously. The invention also provides products for combined non-therapeutic antibacterial use, the products comprising an antibacterial peptide of Formula I or II and one or more surfactants for use separately, sequentially or simultaneously. Where products or compositions are intended for biological use, the one or more surfactant is typically biocompatible. In one aspect, the one or more surfactants comprises the Mx polypeptide as described herein.

Compositions

In one aspect, the invention relates to compositions comprising one or more peptides of Formula I or II of the first or second aspects of the invention.

A composition may be a surfactant-containing composition, or preservative-containing composition such as any of those described herein in relation to peptide use, including pharmaceutical compositions and personal care compositions.

A composition of the invention may be an anti-bacterial composition.

The composition may be for non-therapeutic use (e.g. a disinfectant spray, gel or liquid, a hand wash, a mouth wash, a shampoo, or a cosmetic cream, ointment or spray) or may be a pharmaceutical composition for therapeutic use as described further herein.

Accordingly in one aspect the invention further provides an antibacterial composition comprising a peptide of Formula I or II of the first or second aspects of the invention.

The invention also provides a personal care composition comprising a peptide of Formula I or II of the first or second aspects of the invention.

The invention further provides a pharmaceutical composition comprising a peptide of Formula I or II of the first or second aspects of the invention or a pharmaceutically acceptable salt thereof, in admixture with one or more pharmaceutically acceptable excipients, carriers or diluents.

A pharmaceutical composition comprising a peptide of Formula I or II may be a composition for treating bacterial infection, or for treating cancer, in which the peptide is an active ingredient (antibacterial or anti-tumour). However, as above, the invention also relates to pharmaceutical compositions in which the peptide of Formula I or II is not an active ingredient, but acts as a surfactant or preservative.

A pharmaceutical composition generally includes at least one active ingredient and a pharmaceutically acceptable excipient (e.g. carrier or diluents).

A composition for treating bacterial infection, or for treating cancer, which comprises a peptide of Formula I or II as an active ingredient may additionally include one or more other active agents, for example, one or more other anti-bacterial agents, or one or more other anti-cancer therapeutics.

A composition according to the invention, such as any of those described herein, may comprise one or more peptides of Formula I or II of the first or second aspects of the invention and one or more surfactants, e.g. the Mx polypeptide.

Pharmaceutically acceptable excipients useful in the methods disclosed herein are conventional. Remington's Pharmaceutical Sciences, by E. W. Martin, Mack Publishing Co, Easton, Pa., 15th Edition (1975), describes compositions and formulations suitable for pharmaceutical delivery of the peptides herein disclosed.

Such formulations may further routinely contain pharmaceutically acceptable concentrations of salt, buffering agents, preservatives, antioxidants, compatible carriers, and as above, optionally other therapeutic agents.

The formulations may also include antioxidants and/or preservatives. As antioxidants may be mentioned tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiaretic acid. Suitable preservatives may for instance be phenol, chlorobutanol, benzylalcohol, methyl paraben, propyl paraben, benzalkonium chloride and cetylpyridinium chloride.

A pharmaceutical composition may have a number of different forms depending on, for example, how the composition is to be administered.

Any suitable administration route and/or delivery means may be used to deliver a peptide or a composition to a subject, for example, oral, parenteral, transdermal, intradermal, inter-arterial or intravenous. Administration may be topical. In one example, administration may be by intravenous, inter-arterial or subcutaneous injection or infusion, or by oral administration. In one example, peptide may be administered in the form of a nucleic acid encoding the peptide. Methods for nucleic acid delivery are known in the art.

In one embodiment, a composition is for oral administration. An oral pharmaceutical formulation may be for repeated administration e.g. one a day, two a day or greater frequency. Solid dosage forms for oral administration include capsules, tablets (also called pills), powders and granules. In such solid dosage forms, the active compound is typically mixed with at least one inert, pharmaceutically acceptable excipient or carrier such as sodium citrate or dicalcium phosphate and/or one or more fillers, extenders, humectants, dissolution aids, ionic surface active agents. The active compounds may also be in micro-encapsulated form, if appropriate, with one or more excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers.

In one example, a composition may be for parenteral administration. Parenteral preparations can be administered by one or more routes, such as intravenous, subcutaneous, intradermal and infusion; a particular example is intravenous. A formulation disclosed herein may be administered using a syringe, injector, plunger for solid formulations, pump, or any other device recognized in the art for parenteral administration.

Actual dosage levels of active ingredient (e.g. peptide) in pharmaceutical compositions may be varied so as to obtain an amount of active ingredient that is effective to achieve the desired therapeutic response, for a particular subject, composition, and mode of administration (referred to herein as a "therapeutically effective amount").

The selected dosage level may, for example, depend upon the activity of the particular active ingredient, the severity of the condition being treated and the condition and prior medical history of the patient being treated. However, it is within the skill of the art to start doses at levels lower than required for to achieve the desired effect and to gradually increase the dosage until the desired effect is achieved.

EXAMPLES

The invention will now be described in further detail with reference to the following specific examples.

Examples 1 to 7

Materials and Methods

Peptide Synthesis and Purification

Protected amino acids (Fmoc-Ile-OH, Fmoc-Leu-OH, Fmoc-Lys(Boc)-OH Fmoc-Gly-OH), 2-(1H-benzotriazole-1-yl)-1,1,3,3-tetramethyluronium hexafluorophosphate (HBTU), 1-hydroxybenzotriazole anhydrous (HOBt anhydrous), diisopropyl ethylamine (DIEA), and rink amide MBHA resin were purchased from GL Biochem (Shanghai) Ltd. and used as received. Other reagents and solvents were obtained from Sigma and used without further purification unless otherwise stated. Dichloromethane (DCM) and dimethyl formamide (DMF) were redistilled and subsequently dried with molecular sieves prior to use. The peptides were synthesized by using a standard Fmoc solid-phase strategy form on a commercial CEM Liberty microwave synthesizer. Rink-amide MBHA resin (0.83 mmol/g) was used as support to allow the C-terminus to be amidated. Cleavage from resin and side-chain deprotection were carried out using a mixture of trifluoroacetic acid (TFA), water, triisopropylsilane (TIS) (95:2.5:2.5 v/v) for 3 h at room temperature. The crude peptides were then repeatedly washed with cold ethyl ether at least eight times and then purified by RP-HPLC (>95%).

The identities of the resulting peptides were confirmed by MALDI-TOF mass analysis. For MALDI-TOF mass analysis, the measurements were conducted on Bruker Biflex III matrix assisted laser desorption/ionization time of flight (MALDI-TOF) mass spectrometer equipped with a 337 nm nitrogen laser, and 4-hydroxy-α-cyanocinnamic acid was used as the matrix. The sample was dissolved with the matrix in the mixture of acetonitrile and water (1:1, v/v) containing 1% trifluoroacetic acid. Around 0.5 μl of the sample solution was placed on a metal sample plate and then allowed to air-dry at the ambient temperature around 20° C. Mass spectra were acquired in positive linear mode and using an acceleration voltage of 19 kV. External mass calibration was performed using a standard peptide mixture and the laser power was set close to the threshold of ionization. Generally 100 pulses were acquired and averaged.

N-terminal FITC-labeled G(IIKK)$_3$I-NH$_2$ (SEQ ID NO: 3) was synthesized also by the solid-phase method as reported in Julian et al 2009. Because it is believed that degradation can happen during the latter cleavage process in acidic environment by a mechanism similar to Edman degradation induced by phenylthioisocyanate and yield fluorescein thiohydantoine (FTH) when direct linking FITC at the N-terminal amine of anchored peptides, we introduced 6-aminohexanoic acid (Ahx) between the last amino acid and the thiourea linkage generated through the reaction of isothiocyanate and amine. The detailed procedures were as follows: firstly, the Ahx-G(IIKK)$_3$I-resin (SEQ ID NO: 48) was synthesized on the microwave synthesizer taking the Fmoc-Ahx as amino acid in conjunction with N-terminus amino acid. The fluorescein moiety (Fl) was attached by treating a resin-bound Ahx-G(IIKK)$_3$I (SEQ ID NO: 48) (0.25 mmol) with FITC (1.0 mM) and diisopropyl ethyl amine (DIEA, 5 mM) in 10 ml DMF for 24 h with the exclusion of light. The ninhydrin test was used to check the completion of the reaction. Unreacted FITC molecules were removed via a filter and repeated washing with DCM until the filtrate became clear. The FITC-labeled peptides were then cleaved from the resin using 95:5 TFA/TIS for 3 h at room temperature. The purification of the crude product was similar.

Determining Surface Activity and Penetration into Lipid Monolayers

This experiment was done by applying surface tension measurement from a Langmuir trough to a well-plate, with each well containing 350 µl 10 mMTris buffer solution (also containing 154 mM NaCl). The lipid (DPPC (1,2-dipalmitoyl-sn-glycero-3-phosphocholine) or DPPG (1,2-dipalmitoyl-sn-glycero-3-phospho-glycerol) was loaded by carefully dropping a small drop of chloroform solution with the equilibrated surface pressure initially controlled at 30 mN/m. Peptide solution was then added to reach a final concentration of 3 µM, followed by the subsequent monitoring of surface pressure against time.

Circular Dichroism (CD) Spectroscopy

CD spectra were measured on a Bio-Logic MOS 450 spectrometer using a quartz cell of 1-mm path length. Spectra were recorded from 190-250 nm at a scan speed of 50 nm/min. The peptides were dissolved in water and different phospholipid small unilamellar vesicles (SUVs) which were prepared in 10 mM tris-HCl buffer (pH7.4). In all tests, peptide concentrations were fixed at 0.1 mM. Baseline spectra for each solvent were obtained beforehand. Three scans were averaged to improve the signal to noise ratio. All measurements were carried out at room temperature and the CD data are expressed as mean residual molar ellipticity.

Preparation of Phospholipid SUVs

Two small unilamellar vesicles (SUVs) of different phospholipid compositions, DPPC or DPPG, were prepared by ultrasonic treatment. Typically, dry lipids were dissolved in chloroform in a small glass vessel and the solvents were removed by evaporating in vacuum overnight to form a thin film on the wall of the glass vessel. Dried thin films were rehydrated in 10 mM Tris buffer (Due to the interference for the CD signal of Cl⁻, we used a tiny amount of HF instead of HCl to modulate the pH of the Tris buffer to 7.4) by vortex mixing and the lipid dispersions were then sonicated on ice water for 10 min with a titanium-tip ultrasonicator until the solution became transparent.

Antimicrobial Assay

To determine antibacterial activity of peptides, survival rate curves were constructed. Bacteria (*E. coli* DH5α or *B. subtilis* 168) were incubated with peptide at varying peptide concentrations at 37° C. for 1 h. Aliquots of 2 µL were withdrawn, diluted and spread on agar plates. After overnight incubation at 37° C., the surviving bacteria were expressed as the percentage of total cells, and survival curves drawn (FIG. 4). Controls were bacteria without peptide.

The minimal inhibitory concentrations (MICs) of each peptide were measured by standard microdilution method. The test was done in sterile 96-well plates in a final volume of 200 µL. Aliquots (100 µL) of a bacterial suspension at $1 \times 10^5$ (colony-forming units (CFU)/ml) in culture medium were added to 100 µL peptide solution (2-fold serial dilutions in 10 mM PBS buffer). After incubation with agitation for 18-24 h at 37° C., the inhibition of bacterial growth was assessed by measuring the absorbance at 600 nm with a microplate ELISA reader. The MIC was defined as the lowest concentration of peptide for which there was no visible growth. Each determination was performed at least three times.

Antitumor Activity

Antitumor activities of peptides were measured using the 3-(4,5-dimethylthiazol-2-yl)-2,-diphenyl tetrazolium bromide (MTT) assay, and the $IC_{50}$ value was calculated as the concentration of peptide that induced 50% growth inhibition compared to the untreated control.

HeLa and HL60 cells were seeded in 96-well plates ($10^5$ cells/well) in a complete medium [Iscove's modified dulbecco's medium (IMDM)] with 10% fetal bovine serum (FBS) for 24 h before peptide treatment. The next day, cells were treated with peptides, to give final concentrations of 50, 25, 12.5, 6 and 3 µM, and incubated for another 24 h. Following incubation with peptides, 20 µL of a 5 mg/ml solution MTT reagent was added to each well and incubated for 4 h at 37° C. After removing the supernatant, 150 µL of dimethyl sulfoxide (DMSO) was added to dissolve the formazan crystals that remained in the wells. The absorbance was determined using a microplate ELISA Reader at 570 nm. Wells without cells for blanking the spectrophotometer and the cells without peptides were taken as negative controls.

Hemolytic Activity

Peptide hemolytic activities were measured by determining hemoglobin release by 4% (v/v) suspensions of fresh human erythrocytes at 540 nm. Fresh human red blood cells (hRBCs) from volunteers were centrifuged and washed three times with PBS (pH7.4). 100 µL of hRBCs suspended in PBS at 8% (v/v) were mixed with 100 µL of different series of 2-fold diluted peptides in a sterile 96-well plate. The plates were incubated for 1 h at 37° C., and centrifuged at 1000 g for 5 min. 100 µL aliquots of the supernatant were transferred to new 96-well plates, and hemoglobin release monitored by measuring supernatant absorbance at 540 nm with a microplate ELISA Reader. As negative and positive controls, hRBCs in PBS and 0.1% Triton X-100 were employed. The hemolysis percentage was calculated using the follow equation:

$$\% \text{ hemolysis} = [(Abs_{540\ nm\ with\ peptide} - Abs_{540\ nm\ in\ PBS}) / (Abs_{540\ nm\ with\ 0.1\%\ Triton\ X-100} - Abs_{540\ nm\ in\ PBS})] \times 100$$

Observing Bacterial Membrane Lysis by Fluorescence Microscopy

Peptide G(IIKK)₃I-NH₂ (SEQ ID NO: 3) at its MIC was incubated with *E. coli* or *B. subtilis* bacteria for 1 h, followed by incubation with dyes of DAPI (4',6-Diamidino-2-Phenylindole) and FITC (fluorescein isothiocyanate). The systems were then viewed by fluorescence microscopy. FITC can only enter leaky cells with membrane damages.

Observing Bacterial Membrane Lysis by Scanning Electron Microscopy (SEM)

Peptide G(IIKK)₃I-NH₂ (SEQ ID NO: 3) at its MIC was incubated with *E. coli* or *B. subtilis* bacteria for 1 h. After fixing with 2.5% aldehyde, gradient dehydration, critical drying and gold sputtering, SEM images were taken from these samples.

Assessing Cell Membrane Damage in HeLa Cells by Determining Leakage of Calcein

HeLa cells were first dyed by incubating with calcein-AM (calcein acetoxymethyl ester) dye. 0.1 mM peptide was then added for 30 min, 1 h and 2 h. The top clear solution was removed and residual fluorescence intensity from the cell body was measured (negative control was with PBS and positive control was with 0.1% Triton X100 to provide 0 and 100% release respectively).

Under similar conditions, MTT assays were used to check cell viability so that the extent of cell membrane damage can be linked to cell viability.

Assessing Cell Membrane Damage and Cell Breakdown in HeLa Cells by SEM

HeLa cells was incubated under 10 μM G(IIKK)$_3$I-NH$_2$ (SEQ ID NO: 3) for 24 h$_o$. After fixing, gradient dehydration, critical drying and gold sputtering, SEM images were taken.

Selectivity of G(IIKK)$_3$I-NH$_2$ (SEQ ID NO: 3)

To further verify the selective cytotoxicity of G(IIKK)$_3$-NH$_2$ (SEQ ID NO: 3) in vitro, we added the FITC-labeled G(IIKK)$_3$I-NH$_2$ (SEQ ID NO: 3) to the two co-culture systems containing mammalian cell line NIH 3T3 (model host) and bacteria *B. subtilis* 168 or cancer cell line (HL 60). Specifically, NIH 3T3 cells were cultured at 37° C. with 5% CO$_2$ in IMDM supplemented with 10% FBS. After reaching an over 80% confluence, the cells were transferred into a 6-well plate containing sterile coverslips at bottom to a final concentration of 1×10$^5$ cells/well. After overnight culture at 37° C., the medium was replaced with 1 ml *B. subtilis* 168 suspended in PBS with a density of 1×10$^6$ CFU/ml or 1 ml HL 60 cells suspended in PBS with a density of 1×10$^5$ cells/ml. Meanwhile, FITC-labeled G(IIKK)$_3$I-NH$_2$ (SEQ ID NO: 3) dissolved in the same buffer was also added to each well to the final concentration of 20 μM. After incubation at 37° C. for 1 h, the supernatant containing bacteria or HL 60 cells was separated from adherent cells and transferred into a 1.5 ml Eppendorf tube. Both cells and bacteria were then washed twice with PBS and fixed by 2.5% glutaraldehyde for 1 h at room temperature, separately. Finally, 20 μL suspension of the bacteria or HL 60 cell suspensions was dropped onto the coverslip and the location of FITC-labeled G(IIKK)$_3$I-NH$_2$ (SEQ ID NO: 3) was observed with a Nikon TS100-F fluorescence microscopy equipped with an oil immersion lens.

Results

Example 1

Design, Synthesis and Physical Properties of a Series of Cationic Peptides

Nine peptides (Helix-1 to Helix-9) were designed as listed in Table 1 below.

TABLE 1

List of antibacterial peptides studied

| Code | SEQ ID NO: | Sequence | No. of amino acids | Cationic Charges | Estimates of fully stretched backbone lengths/Å |
|---|---|---|---|---|---|
| Helix-1 | 1 | G(IIKK)I-NH$_2$ | 6 | 3 | 20 |
| Helix-2 | 2 | G(IIKK)$_2$I-NH$_2$ | 10 | 5 | 30 |
| Helix-3 | 3 | G(IIKK)$_3$I-NH$_2$ | 14 | 7 | 42 |
| Helix-4 | 4 | G(IIKK)$_4$I-NH$_2$ | 18 | 9 | 54 |
| Helix-5 | 5 | G(LLKK)$_3$L-NH$_2$ | 14 | 7 | 42 |
| Helix-6 | 6 | G(VVKK)$_3$V-NH$_2$ | 14 | 7 | 42 |
| Helix-7* | 7 | G(IIOO)$_3$I-NH$_2$ | 14 | 7 | 42 |
| Helix-8 | 8 | GKI(KKII)$_2$KII-NH$_2$ | 14 | 7 | 42 |
| Helix-9 | 9 | GIK(KKII))$_2$KII-NH$_2$ | 14 | 7 | 42 |

*O in helix-7 is ornithine (Orn), a cationic amino acid as described herein.

The peptides were synthesized by solid-phase peptide synthesis on Rink amide MBHA resin as in the Materials and Methods, and were all purified to >95% homogeneity.

All of the peptides were capped with Gly at the N-terminus and amidation at the C-terminus which were believed to not only provide resistance to peptidases, but also favour α-helical hydrogen bonding (Tossi et al 1997; Tossi et al 2000). In the peptides, the left C terminal is unblocked, thus with 1 cationic charge. Herein, the right terminal NH$_2$ blocking may be abbreviated—for example, G(IIOO)$_3$I-NH$_2$ (SEQ ID NO: 7) may be written as G(IIOO)$_3$I (SEQ ID NO: 7)). The molecular mass (MW) of each peptide was confirmed by MALDI-ToF MS (Table 2 below).

TABLE 2

The masses of the synthetic peptides used

| SEQ ID NO: | Peptides | Theoretical MW | Actual MW/[M ± H] |
|---|---|---|---|
| 1 | G(IIKK)I-NH$_2$ | 669.9 | 670.5 |
| 2 | G(IIKK)$_2$I-NH$_2$ | 1152.6 | 1153.2 |
| 3 | G(IIKK)$_3$I-NH$_2$ | 1635.2 | 1635.6 |
| 4 | G(IIKK)$_4$I-NH$_2$ | 2117.9 | 2117.9 |
| 5 | G((LLKK)$_3$L-NH$_2$ | 1635.2 | 1635.5 |
| 6 | G(VVKK)$_3$V-NH$_2$ | 1537.1 | 1537.5 |
| 7 | G(IIOO)$_3$I-NH$_2$ | 1550.1 | 1551.5 |
| 8 | GKI(KKII)$_2$KII-NH$_2$ | 1635.2 | 1635.1 |
| 9 | GIK(KKII))$_2$KII-NH$_2$ | 1635.2 | 1635.1 |

None of the samples studied had peaks that would indicate the presence of impurities.

A Schiffer-Edmundson wheel projection of helical peptides 2, 3, 4, 8 and 9 was made (FIG. 1).

Helical peptides 1-4 (the G(IIKK)$_n$I-NH$_2$, n=1-4 (SEQ ID NO: 23) series) were examined for surface activity and penetration into lipid monolayers (DPPC or DPPG), as described in the Materials and Methods. As shown in FIG. 2, the peptides interact more strongly with the negatively charged DPPG than the zwitterionic DPPC, resulting in greater surface pressure rise.

Circular dichroism (CD) spectroscopy was used to assess the folded structures of peptides 1-4 in aqueous solution and in membrane-mimetic lipid vesicles (DPPC or DPPG) as in the Materials and Methods.

Figure 3B:
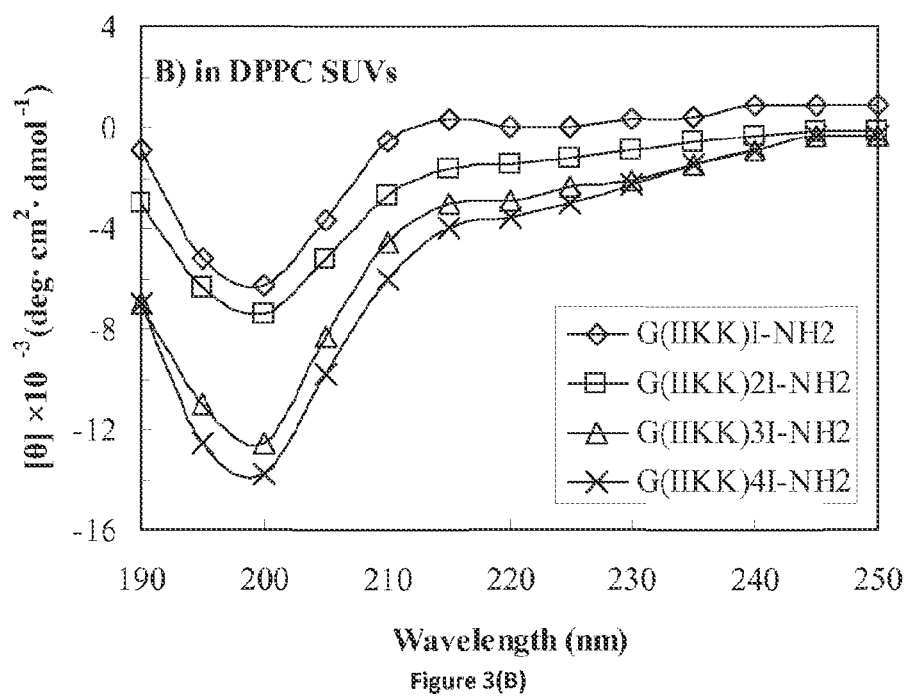

The peptides were unfolded in the aqueous solution (FIG. 3A) due to the considerable inter-molecular hydrogen bonding between peptide backbones and the solvent molecules and also the intra-molecular cationic repulsion between the neighboring lysine residues. In the zwitterionic DPPC (1,2-dipalmitoyl-sn-glycero-3-phosphocholine) SUVs, mimicking normal mammalian host cell membranes, all of the peptides remained unstructured (FIG. 3B).

Figure 3C:
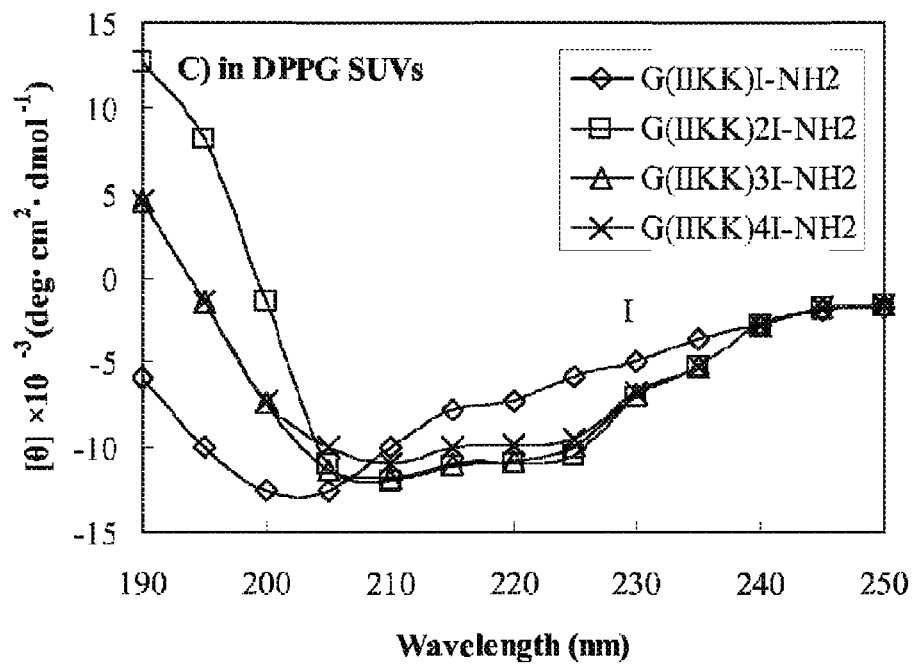

In the negatively charged DPPG (1,2-dipalmitoyl-sn-glycero-3-phospho-glycerol) small unilamellar vehicles (SUVs) mimicking bacterial and tumor cell membranes, all the peptides except G(IIKK)I-NH$_2$ (SEQ ID NO: 1) adopted the typical α-helix structure, with minimal mean residual molar ellipticity values at 208 and 222 nm (FIG. 3C). Thus there is clear structural change due to interaction with the lipid vesicles.

All other helical peptides studied showed similar structural responses upon exposure to the two lipid SUVs. Propensity to form helical structure was found to increase with peptide length.

Thus the CD measurements unraveled not only the delicate interplay between hydrophobic effect, charge interaction and hydrogen bonding crucial for the helix formation, but also the molecular basis of peptide selectivity between different cell membranes.

Example 2

Testing Antimicrobial Activity of the Peptides

The antimicrobial activities of the peptides were measured against gram-negative *Escherichia coli* (*E. coli* DH5α) and gram-positive *Bacillus subtilis* (*B. subtilis* 168).

Survival rate curves were constructed for peptides 1-4 as in the Materials and Methods. Results are shown in FIG. 4.

MIC (minimal inhibitory concentration: the lowest peptide/drug concentration to inhibit bacterial growth) values were determined for each of peptides 1-9, also as described in Materials and Methods. Results are shown in Table 3 (FIG. 7) with results for two natural antibacterial peptides (magainin-2 and melittin), antibiotic ampicillin, and anticancer drug cisplatin cited for comparison.

G(IIKK)I-NH$_2$ (SEQ ID NO: 1) has the weakest activity and it did not show much antimicrobial effect even up to the concentration of 1 mM, consistent with its short length (n=1) and lack of structural responses. The bactericidal activity increased significantly with increasing peptide length or repeat unit, consistent with the enhanced helical structuring, amphipathicity and cationicity.

G(IIKK)$_3$I-NH$_2$ (SEQ ID NO: 3) and G(IIKK)$_4$I-NH$_2$ (SEQ ID NO: 4) are particularly effective against both bacteria, with MICs in the range of 0.5-8 μM. These MIC values are highly comparable to those of melittin and ampicillin with MICs around 2-10 μM, making them as potent as many natural AMPs and commercial antibiotics (Dathe et al 2001, Cruciani et al 1991, Wieprecht et al 1997, Asthana et al 2004, Greenwood et al 1970). The designed peptides are more effective against gram-positive $B.$ $subtilis$ than gram-negative $E.$ $coli$. This trend is similar to Melittin and Ampicillin but the designed peptides are more effective.

Example 3

Testing Antitumor Activity of the Peptides

Antitumor activity of the peptides was measured in HeLa and HL60 cancer cell lines, as described in the Materials and Methods. Survival rate curves for peptides 1-4 are shown in FIG. 5. IC50 values (peptide concentration causing 50% tumor cell growth inhibition) for peptides 1-9 are shown in Table 3 (FIG. 7) with results for two natural antibacterial peptides (magainin-2 and melittin), antibiotic ampicillin, and anticancer drug cisplatin cited for comparison.

The peptides show high activities against tumor cells. The antitumor results assessed from HeLa and HL60 cancer cell lines show similar trend to antibacterial activities with the strength increasing with n in the series G(IIKK)$_n$I-NH$_2$, n=1-4 (SEQ ID NO: 23) (FIG. 7 (Table 3)).

G(IIKK)I-NH$_2$ (SEQ ID NO: 1) has the weakest activity and it did not show much antitumor effect even up to the concentration of 1 mM, consistent with its short length (n=1) and lack of structural responses.

G(IIKK)$_3$I-NH$_2$ (SEQ ID NO: 3), G(IIKK)$_4$I-NH$_2$ (SEQ ID NO: 4), GKI(KKII)$_2$KII-NH$_2$ (SEQ ID NO: 8) and G(IIOO)$_3$I-NH$_2$ (SEQ ID NO: 7) show high potency against both types of cancer cell lines, with IC$_{50}$ values in the 4-25 μM range (FIG. 7 (Table 3)). The activities of G(IIKK)$_4$I-NH$_2$ (SEQ ID NO: 4) and G(IIOO)$_3$I-NH$_2$ (SEQ ID NO: 7) against HeLa cells are comparable to Cisplatin, one of the most widely used and potent chemotherapeutic agents against cancers (Takara et al 2006).

Example 4

Testing Hemolytic Activity of the Peptides in Human Red Blood Cells

The peptides were tested for toxicity against normal host cells by assessing hemolytic activity in human red blood cells.

Hemolytic activity was determined using fresh human red blood cells (hRBCs) as described in the Materials and Methods. Dose-response curves for the hemolytic activities of peptides 1-5 and 8 are shown in FIG. 6. EC50 values (concentration to cause 50% lysis of erythrocytes) for peptides 1-9 are shown in FIG. 7 (Table 3), with results for two natural antibacterial peptides (magainin-2 and melittin), antibiotic ampicillin, and anticancer drug cisplatin cited for comparison.

The broad trend is similar to that found in antimicrobial and antitumor activities, that is, potency increases with increasing n in the series G(IIKK)$_n$I-NH$_2$, n=1-4 (SEQ ID NO: 23). Importantly, however, over the active concentration ranges against bacteria and cancer cells, there is little activity or toxicity against hRBCs. This feature is important for the therapeutic application of the peptides.

Specifically, the two short peptides G(IIKK)I-NH$_2$ (SEQ ID NO: 1) and G(IIKK)$_2$I-NH$_2$ (SEQ ID NO: 2) are inactive up to 250 μM. Although peptide G(IIKK)$_3$I-NH$_2$ (SEQ ID NO: 3) showed some hemolytic activity, it only caused less than 10% hemolysis of erythrocytes at 10-fold MIC (80 μM) against $E.$ $coli$ and very little hemolysis at 10-fold MIC (20 μM) against $B.$ $subtilis$. G(IIKK)$_4$I-NH$_2$ (SEQ ID NO: 4) had the greatest hemolytic activity in the G(IIKK)$_n$I-NH$_2$ n=1-4 (SEQ ID NO: 23) series studied, producing ~25% lysis of erythrocytes at the 10-fold MIC (20 μM) against $E.$ $coli$. Overall, G(IIKK)$_3$I-NH$_2$ (SEQ ID NO: 3) offers an optimal selectivity against bacteria and cancer cells whilst its toxicity to hRBCs remained low, reflecting the balance of the effects of peptide length. Disruption to the hydrophobic helical surface when using GKI(KKII)$_2$KII-NH$_2$ (SEQ ID NO: 8) led to the improvement in hemolysis with similar antibacterial activities particularly against the performance of G(IIKK)$_4$I-NH$_2$ (SEQ ID NO: 4). G(IIOO)$_3$I-NH$_2$ (SEQ ID NO: 7) showed the best selectivity, evident from the lowest MICs and lowest IC50 with the highest EC50 among the best performing ones.

Example 5

Examining Antibacterial Mechanism

Membrane lysis in $E.$ $coli$ and $B.$ $subtilis$ cells, in the presence of G(IIKK)$_3$I-NH$_2$ (SEQ ID NO: 3), was observed by fluorescence microscopy and scanning electron microscopy (SEM) as described in the Materials and Methods.

Results are shown in FIGS. 8 (fluorescence) and 9 (SEM). Fluorescent dye can be seen in the bacterial cells after incubation with the peptides, indicating membrane damages leading to cell breakdown.

Example 6

Examining Antitumor Mechanism

Cell membrane damage in HeLa cells in the presence of peptides 1-4 was determined by measuring leakage of calcein, as described in the Materials and Methods. MTT assays were carried out under the same conditions as described herein, so that the extent of membrane damage could be compared to cell viability. Results are shown in FIG. 10.

Membrane damage and cell breakdown in HeLa cells in the presence of G(IIKK)$_3$I-NH$_2$ (SEQ ID NO: 3) was also assessed by SEM as described herein. Results are in FIG. 11, which illustrates membrane meltdown (B), local membrane damage (C), and apoptosis (D).

Example 7

Co-Culturing to Determining Cell Selectivity of the Peptides

To further confirm the selective responses and cytotoxicity of the peptides, FITC-labeled G(IIKK)$_3$I-NH$_2$ (SEQ ID NO: 3) was synthesized according to the method described previously by Jullian M, et al (Julian et al 2009). The labeled peptide was added into two co-culture systems containing both bacteria (*B. subtilis* 168) or HL60 cancer cells and model host mammalian cells (NIH 3T3) (see Materials and Methods). After incubation for 1 hour, the distribution of FITC-G(IIKK)$_3$I-NH$_2$ (SEQ ID NO: 3) was observed using fluorescence microscopy and the results are shown in FIG. 12. In the images, adherent cells are NIH 3T3, rod-like cells are *B. subtilis*, and round suspension cells are HL60, as marked by black arrows.

As shown, the green fluorescence of FITC-G(IIKK)$_3$I-NH$_2$ (SEQ ID NO: 3) was concentrated in the bacterial clusters or the HL60 cells but not in any part of the 3T3 cells. This further confirms that G(IIKK)$_3$I-NH$_2$ (SEQ ID NO: 3) shows fast responses and highly effective recognition of pathogenic bacteria and the tumor cells in the co-culture environment, with no binding or association to the model host cells. Such a co-culture system can mimic the in vivo infected environment better than commonly used parallel assays.

Examples 8 to 14

Further investigations into the effects of surfactants and polymers as additives on the antibacterial activities of the peptides of the present invention and their toxicities to human dermal fibroblast cells were performed. Such antibacterial peptides have applications in diverse areas including a range of personal care products.

Surfactants and surface active polymers are needed in almost all product formulations including skin and hair care, and many pharmaceutical formulations. Their functions are varied, from helping disperse active ingredients and providing system's stabilisation to enhancing product performance. However, addition of surface active species may alter the antibacterial performance of the short designed peptides. It is hence useful to assess the formulation compatibility. Surface active or surface activity in this work refers to the ability of surfactant or polymer to reduce surface tension, possessing the ability to adsorb at interface or replace other surface active species that have already adsorbed at interface. On the other hand, the current experimental setup also provides a systematic assessment of the biocompatibility of systems containing surfactants and surface active polymers.

Materials

Peptides: a list of short designed antibacterial peptides investigated:
G2=G(IIKK)$_2$ I-NH$_2$ (helix-2) (SEQ ID NO: 2);
G3=G(IIKK)$_3$ I-NH$_2$ (helix-3) (SEQ ID NO: 3);
G4=G(IIKK)$_4$ I-NH$_2$ (helix-4) (SEQ ID NO: 4);
GO=G(IIOO)$_3$ I-NH$_2$ (helix-7) (SEQ ID NO: 7);
GKI=GKI(KKII)$_2$ KII-NH$_2$ (helix-8) (SEQ ID NO: 8);
GIK=GIK(KKII)$_2$ KII-NH$_2$ (helix-9) (SEQ ID NO: 9);
GL=G(LLKK)$_3$ L-NH$_2$ (helix-5) (SEQ ID NO: 5).

Mammalian cells: the main human skin cells used were the fibroblast cells, Neonatal (HDFn) and Adult (HDFa) obtained from Invitrogen. Under almost all these studies, parallel measurements were made using 3T3 fibroblast cell line for direct comparison. The medium used was M106 supplemented with low serum growth supplement (LSGS), amoxicillin and penicillin antibiotics. The MTT (Thiazolyl Blue Tetrazolium Bromide) used in this experiment for viability assessment was bought from SIGMA Cat. No: M565.

Bacteria: the main microorganisms used within this investigation were Gram-negative *Escherichia coli* or *E. coli*, (EC) and Gram-positive bacteria strain *Staphylococcus aureus* or *S. aureus*, (SA). They were incubated in LB (Luria-Bertani) medium.

Surfactants: Most cosmetic products contain ingredients including surfactants, thickeners and foaming agents. Here we have tested a number of surfactants in order to investigate their influence on antibacterial effect and cytotoxicity to human cells. The surfactants investigated were cationic (Dodecyl trimethylammonium bromide, C12TAB), anionic (Sodium dodecyl sulphate, SDS) and non-ionic surfactants (Pentaethylene glycol monododecyl ether, C12E5; Hexaethylene glycol monododecyl ether, C12E6), non-ionic polymers (PLURONIC; commercially available Ethylene Oxide/Propylene Oxide Block Copolymer P123, triblock copolymer manufactured by the BASF Corporation F127) and a commercial mixture of surfactants (BYOTROL-antibacterial hand wash). Some common cosmetic ingredients included in the investigation were cocamide ethanolamines (CMEA, a milky white foaming agent, COMPERLAN 100); cocamidopropyl aetaine (Tt, an amphoteric detergent, TEGO BETAIN); sodium lauryl ether sulphate (SLES, a foaming agent and detergent, TEXAPON N 701).

Novel polypeptides tested were derived from egg shell membranes, a small molecular weight one (SL, with molecular weight distribution centred around 5-10 kDa) and a mixed large molecular weight one (Mx, with molecular weight distribution centred around 30-40 kDa). Also, a further natural peptide used was obtained from silk worm cocoons with molecular weight distribution over 10 kDa. All these peptides were thus highly mixed polymers and were water soluble under physiological conditions tested. For the sake of clarity, these peptides are termed polypeptides.

MTT assay: Cell viability and proliferation is widely assessed by the MTT assay as already described previously.

RT-PCR (Reverse Transcription Polymerase Chain Reaction and Real Time Polymerase Chain Reaction): To determine the related gene transcriptional activities about HeLa cell apoptosis and the lymphocyte immunological effects, RT-PCR assays were performed. Briefly, HeLa cells were incubated with 10 µM G(IIKK)$_3$I-NH$_2$ (SEQ ID NO: 3) for different time intervals (1, 3, 6 and 12 h) and lymphocytes were incubated with 10 µM G(IIKK)$_3$I-NH$_2$ (SEQ ID NO: 3) for 1 h. Total RNA from the cells was extracted by Trizol following the manufacturer's instructions (Invitrogen, Britain). Total RNA (1 µg) was subject to cDNA synthesis with random primers (PrimeScript Reverse Transcriptase, Takara, Japan). Real-Time PCR was performed with power SYBR green PCR Master Mix kit (Applied Biosystems, American) using a 7500 real-time PCR system (Applied Biosystems, American) according to the protocol of the manufacturer, and the data were analyzed by relative quantitation of the $2^{-\Delta\Delta Ct}$ method. Transcriptional levels of related genes were normalized to the values of the house keeping gene β-actin. The following primers were used: β-actin sense: 5'-ATGCCAGGGTACATGGTGGT-3' (SEQ ID NO: 10), antisense: 5'-TCGTGCGTGACATTAAGGAG-3' (SEQ ID NO: 11); aspase-8 sense: 5'-ATGGACTTCAGCA GAAATCTT-3' (SEQ ID NO: 12), antisense: 5'-CATGTCATCATCCA-GTTTGC-3' (SEQ ID NO: 13); fas sense: 5'-ATTATCGTC- CAAAAGTGTTA-3' (SEQ ID NO: 14), antisense: 5'-TCA-CACAATCTACATCTT CTG-3' (SEQ ID NO: 15); fasL sense: 5'-ATGCAGCAGCCCTTCAATTAC-3' (SEQ ID NO: 16), antisense: 5'-CAATCCTACCAAGGCAACC-3' (SEQ ID NO: 17); IL2 sense: 5'-CACATTAACCT-CAACTCC TGCCAC-3' (SEQ ID NO: 18), antisense: 5'-CGTTGATATTGCTGATTAAGTCCCTG-3' (SEQ ID NO: 19); IL8 sense: 5'-CGGAAGGAACCATCTCACT-GTG-3' (SEQ ID NO: 20), antisense: 5'-AGAAATCAG-GAAG GCTGCCAAG-3' (SEQ ID NO: 21).

Example 8

Peptide Antibacterial Activities

Bacteria E. coli, (EC) and S. aureus, (SA) were grown in LB media at 37° C. with continuous shaking for 24 hours. The bacterial concentration was then adjusted such that the absorbance at 600 (A600) was controlled to ca 0.2 unit. The bacteria suspensions with the peptides were incubated in 96-well tissue culture plates. The total medium volume in each well was 200 4. Concentrations of 25, 50 and 100 µM were used for each of the seven peptides and ampicillin (beta-lactam antibiotic) was used as a standard reference. Controls with media only and media with bacteria only were run alongside the peptide bacteria mixed suspensions. Measurements were taken at time t=0, t=20 and t=72 hours using optical density cell plate reader. The optical density (OD) is representative of the relative amount of bacterial growth within the medium.

Figure 13A:
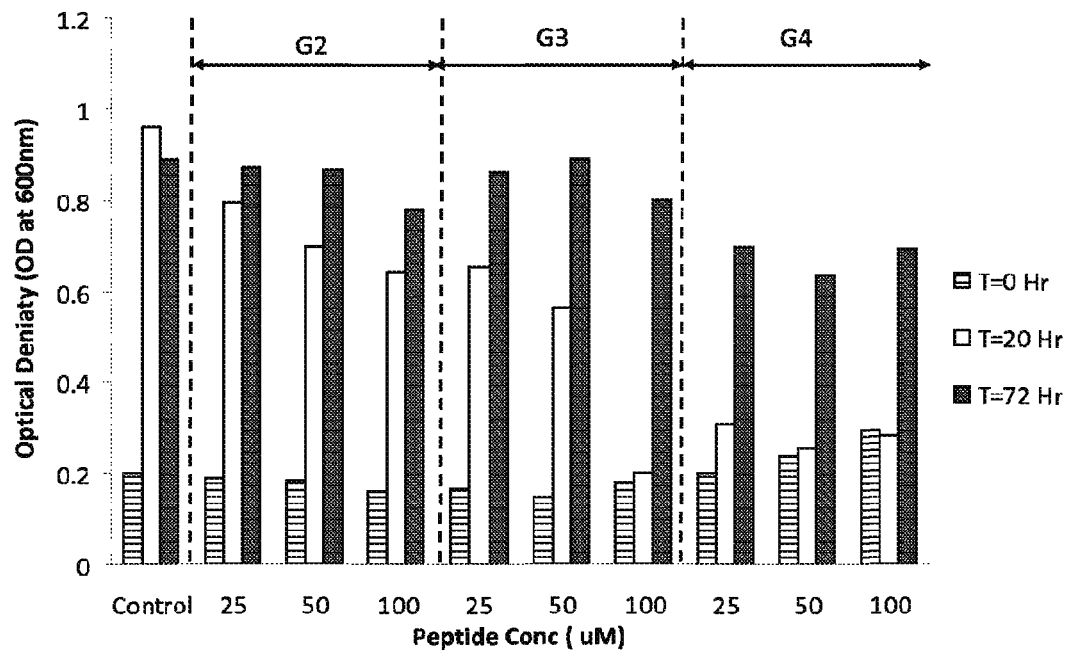
FIGS. 13 (*a*) to (*c*)—The antibacterial activity of the seven peptides described in reference to Example 8 and ampicillin against the Gram-negative bacteria *E. coli*, (EC).
Figure 13B:
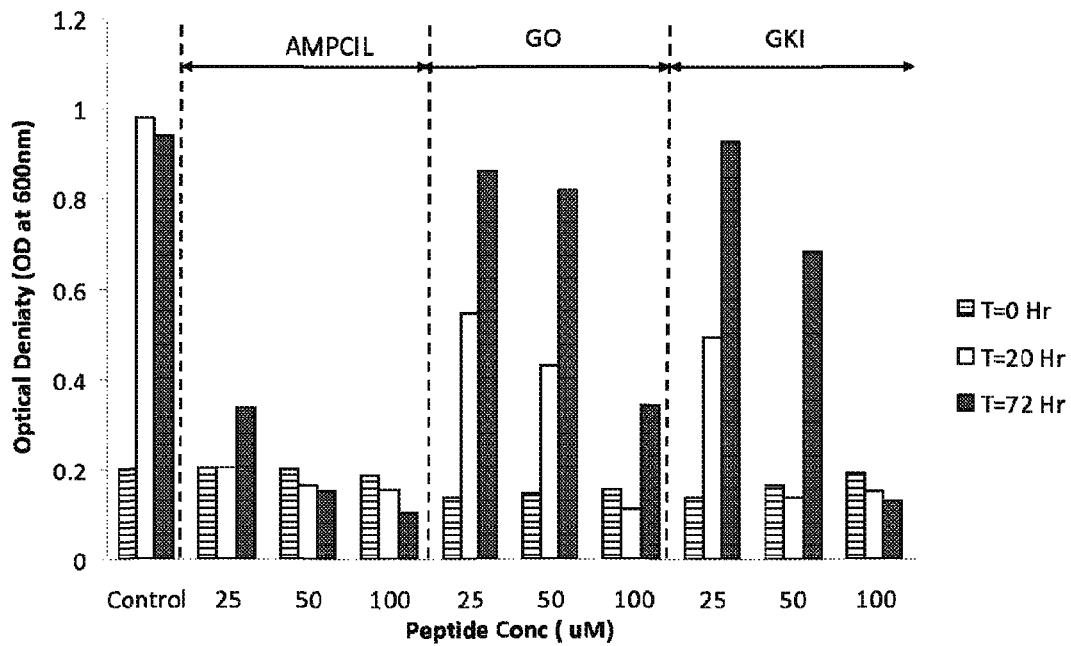
Figure 13C:
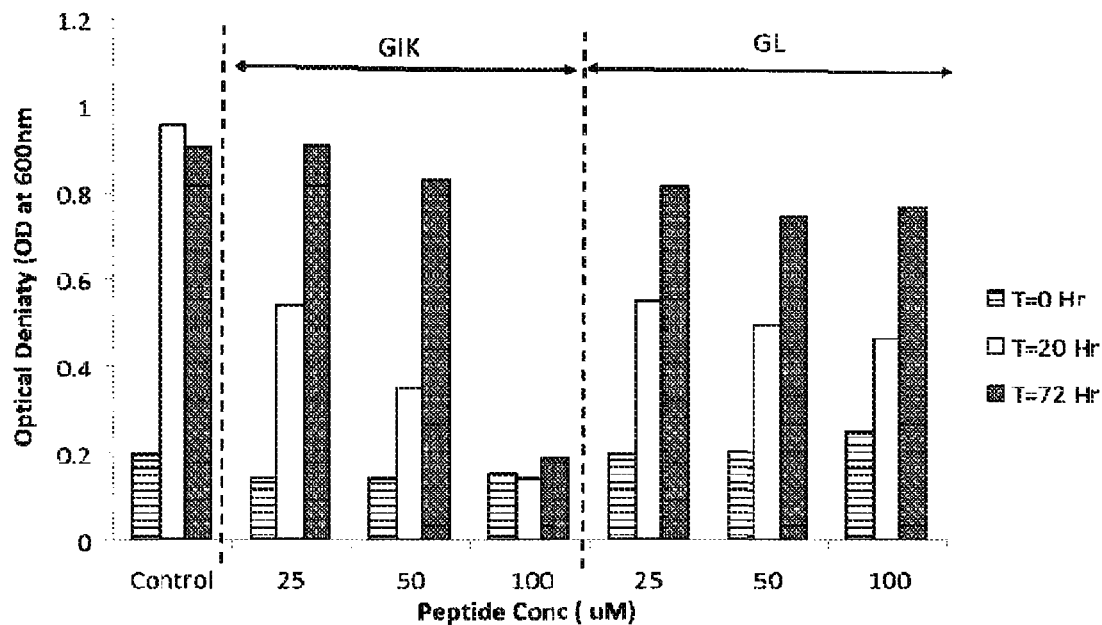
Figure 14A:
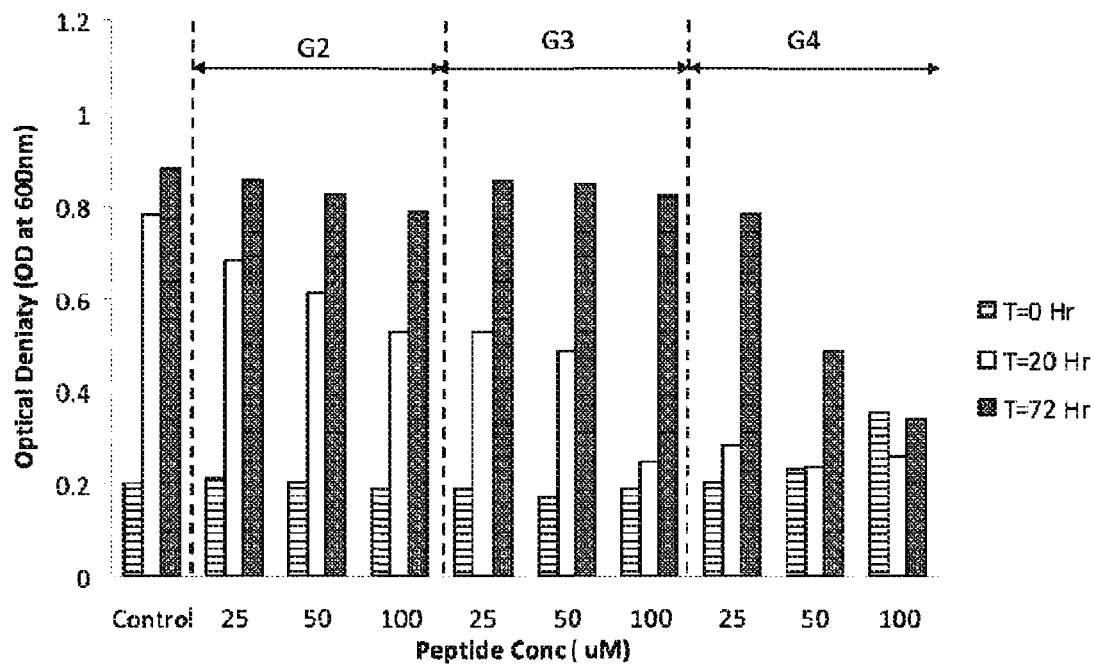
FIGS. 14 (*a*) to (*c*)—The antibacterial activity of the seven peptides described in reference to Example 8 and ampicillin against the Gram-positive bacteria *S. aureus*, (SA).
Figure 14B:
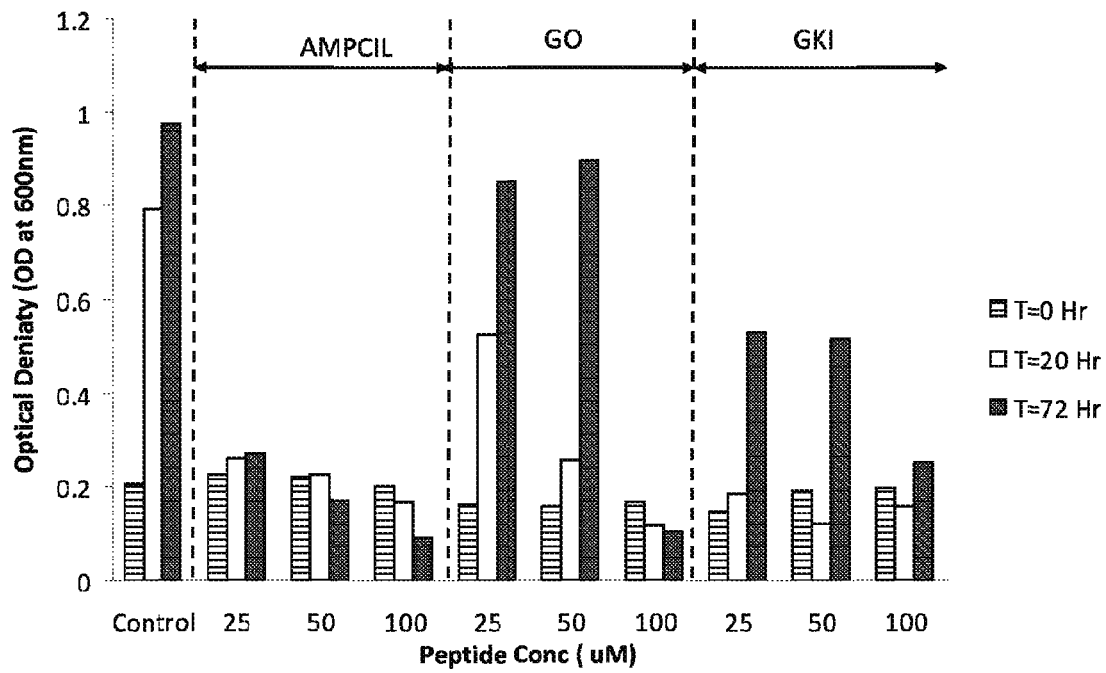
Figure 14C:
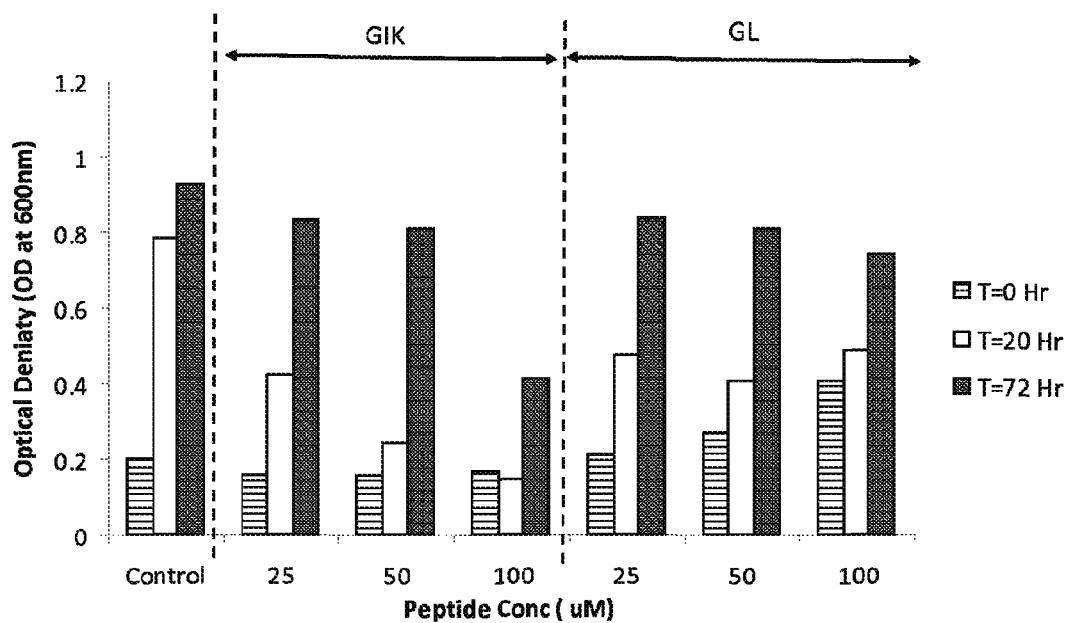

Results are presented in FIGS. 13 and 14. The bacterial growth after 20 hours within the control (without any antibacterial agent) was almost unity. In comparison, the growth of bacteria within the wells containing antibiotic agents was reduced at t=20 hours, indicating clear antibiotic activity of the peptides. For all the designed short peptides there was greater antibacterial effect as the peptide concentration was increased from 25 µM to 100 µM. The peptide G2 was shown not to be a very effective antibacterial peptide. However, as IIKK (SEQ ID NO: 24) units increased from 2 to 3 and 4 in G3 and G4 peptides respectively, the antibacterial activity was significantly improved. The G4 peptide was shown to be effective at even the low concentration of 25 µM against both S. aureus and E. coli. In contrast, G3 was only effective at the higher concentration of 100 µM. GL had some antibacterial activity, but this was not improved much by increasing its concentration. Relative to the activity of ampicillin, the most effective antibiotic peptides were found to be G4, GO, GKI and GIK. These were selected for further investigation with cells and surfactants.

Example 9

Interactions of Human Cells with Designed Short Peptides

The fibroblasts cells, Neonatal (HDFn) and Adult (HDFa), were both grown until greater than 80% confluent. The cells were then harvested and seeded into micro well plate at cell densities of 5000 cells/well in a volume 100 4 of medium. After 24 hour incubation the culture medium was replaced with fresh medium containing an appropriate amount of the peptide for investigation. Control wells containing medium with cells but no peptide and blank wells with medium only were also included to calculate the MTT results. Peptide concentrations of 5, 25, 50 and 100 µM were prepared and for comparison ampicillin was also included in the experiment.

The viability of the cells in the presence of the peptides was tested by MTT assay over three days. The results are shown for fibroblasts cells Adult (HDFa) and Neonatal (HDFn) in Table 4 and Table 5, respectively. For all peptides, at concentration of 25 µM and below, the viability of both fibroblasts (HDFa and HDFn) was comparable to that of ampicillin. In the presence of 50 µM peptide the viability of both cells was reduced by up to 10-25%, in particular by day three. For peptides GL and G4 this reduction in viability was significantly larger in both HDFa and HDFn. For all peptides at the concentration of 100 µM, the viability for HDFa and HDFn cells was further reduced by up to 20%-30%. Again, G4, GIK and in particular GL were found to be significantly more toxic to the cells. Similar results were observed from 3T3 fibroblast cells.

TABLE 4

MTT results for fibroblasts Adult (HDFa) cells at four different peptide concentrations over three days. Low MTT readings indicate low viability. Changes in relative MTT readings indicate varying cell viabilities against time and peptide concentration. The peptide nomenclatures are indicated previously in the Materials section.

| | Peptide | | | | | | | | | | | | | | | |
|---|---|---|---|---|---|---|---|---|---|---|---|---|---|---|---|---|
| | G2 | | | | G3 | | | | G4 | | | | Ampicillin | | |
| | Conc (µM) | | | | | | | | | | | | | | | |
| | 5 | 25 | 50 | 100 | 5 | 25 | 50 | 100 | 5 | 25 | 50 | 100 | 25 | 50 | 100 |
| Day 1 | 1.01 | 0.98 | 0.92 | 0.91 | 0.91 | 0.88 | 0.87 | 0.78 | 0.90 | 0.87 | 0.85 | 0.81 | 0.97 | 1.01 | 1.00 |
| Day 2 | 0.96 | 0.90 | 0.90 | 0.88 | 0.92 | 0.85 | 0.84 | 0.75 | 0.84 | 0.81 | 0.78 | 0.70 | 1.01 | 1.02 | 1.01 |
| Day 3 | 0.95 | 0.88 | 0.79 | 0.80 | 0.81 | 0.80 | 0.75 | 0.71 | 0.81 | 0.78 | 0.65 | 0.55 | 0.79 | 0.85 | 0.85 |
| | Peptide | | | | | | | | | | | | | | | |
| | GO | | | | GKI | | | | GIK | | | | GL | | | |
| | Conc (µM) | | | | | | | | | | | | | | | |
| | 5 | 25 | 50 | 100 | 5 | 25 | 50 | 100 | 5 | 25 | 50 | 100 | 5 | 25 | 50 | 100 |
| Day 1 | 1.01 | 0.98 | 0.95 | 0.88 | 0.95 | 0.93 | 0.90 | 0.85 | 0.97 | 0.92 | 0.87 | 0.85 | 0.91 | 0.90 | 0.87 | 0.63 |
| Day 2 | 0.95 | 0.92 | 0.83 | 0.75 | 0.82 | 0.81 | 0.80 | 0.75 | 0.95 | 0.93 | 0.78 | 0.74 | 0.90 | 0.88 | 0.75 | 0.57 |
| Day 3 | 0.90 | 0.82 | 0.78 | 0.70 | 0.81 | 0.75 | 0.71 | 0.70 | 0.91 | 0.90 | 0.73 | 0.65 | 0.87 | 0.74 | 0.46 | 0.11 |

TABLE 5

MTT results for fibroblast Neonatal (HDFn) cells at four different peptide concentrations over three days. Low MTT readings indicate low viability. Changes in relative MTT readings indicate varying cell viabilities against time and peptide concentration. The peptide nomenclatures are indicated previously in the Materials section.

| | Peptide | | | | | | | | | | |
|---|---|---|---|---|---|---|---|---|---|---|---|
| | G4 | | | | GKI | | | | Ampicillin | | |
| | Conc (μM) | | | | | | | | | | |
| | 5 | 25 | 50 | 100 | 5 | 25 | 50 | 100 | 25 | 50 | 100 |
| Day 1 | 0.95 | 0.85 | 0.81 | 0.73 | 0.95 | 0.87 | 0.81 | 0.69 | 1.04 | 0.97 | 1.01 |
| Day 2 | 0.92 | 0.77 | 0.71 | 0.65 | 0.90 | 0.83 | 0.75 | 0.60 | 0.98 | 1.01 | 1.02 |
| Day 3 | 0.79 | 0.74 | 0.65 | 0.53 | 0.88 | 0.78 | 0.71 | 0.55 | 0.87 | 0.90 | 0.87 |

| | Peptide | | | | | | | | | | |
|---|---|---|---|---|---|---|---|---|---|---|---|
| | GO | | | | GL | | | | GIK | | |
| | Conc (μM) | | | | | | | | | | |
| | 5 | 25 | 50 | 100 | 5 | 25 | 50 | 100 | 5 | 25 | 50 | 100 |
| Day 1 | 0.95 | 0.91 | 0.88 | 0.83 | 0.98 | 0.88 | 0.85 | 0.80 | 0.93 | 0.98 | 0.92 | 0.85 |
| Day 2 | 0.91 | 0.85 | 0.81 | 0.75 | 0.87 | 0.84 | 0.74 | 0.65 | 0.87 | 0.84 | 0.81 | 0.78 |
| Day 3 | 0.85 | 0.80 | 0.75 | 0.65 | 0.83 | 0.81 | 0.67 | 0.35 | 0.83 | 0.78 | 0.75 | 0.71 |

Example 10

Surfactant Interactions with Cells

The viability of the fibroblasts, Adult (HDFa) and Neonatal (HDFn) cells in the presence of surfactants was tested by MTT assay over three days relative to control wells containing cells only. The results are shown in Table 6 for HDFa with all surfactants tested. The data shows that the cells cannot survive in the presence of the selected cationic, anionic or non-ionic surfactants. This was also true for the commonly used surfactants, SLES, CMEA and Tt. Popularly used surface active polymers tend to show the same trend. In contrast to this outcome, the polymeric surfactant that did not cause a major cytotoxicity to these mammalian cells was pluronic F127. Systems containing egg shell membrane derived polypeptides and silk polypeptides as additives showed high compatibility with the fibroblast cells, that is, these polypeptides did not cause any major inhibition to cell growth against control. Similar trends were observed when Neonatal (HDFn) fibroblast cells were used.

Example 11

Surfactant Interactions with Bacteria

Interactions of bacteria *E. coli*, (EC) and *S. aureus*, (SA) with surfactants were also studied. The bacteria were grown in LB media at 37° C. with continuous shaking for 24 hours. The bacterial concentration was then adjusted such that the absorbance at 600 (A600) was controlled at ca 0.2 unit. The bacteria suspensions with surfactants were incubated in 96-well tissue culture plates. The total medium volume in each well was 200 μL. Again, surfactant concentrations of 1% were used. Controls with media only and media with bacteria only were run alongside the surfactant-bacteria mixed suspensions. Measurements were taken at time t=0, t=20 and t=72 hours using optical density cell plate reader again.

Figure 15:
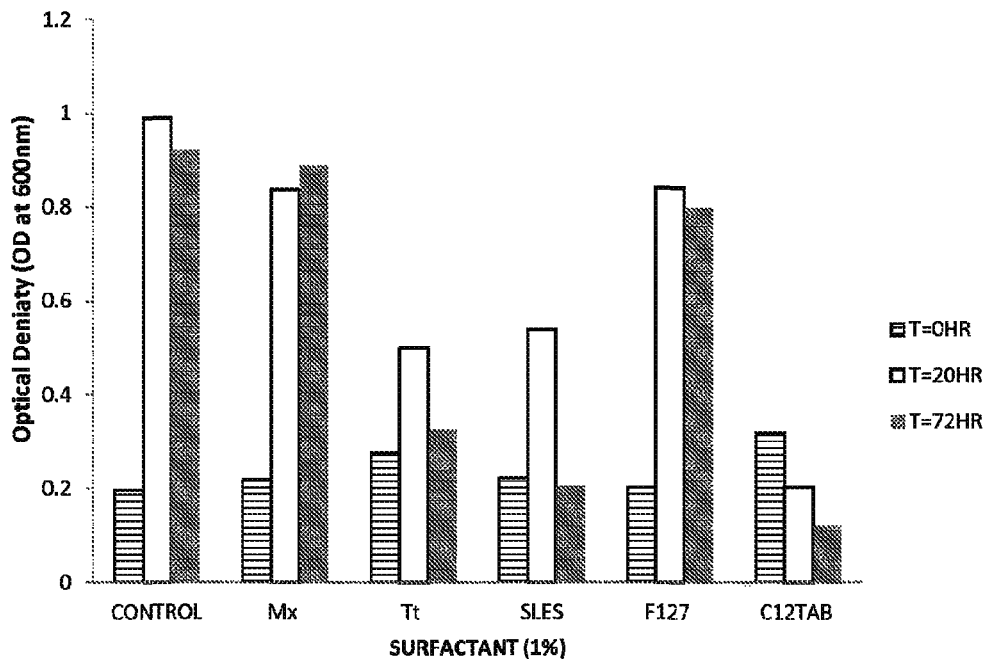
FIG. 15 Interactions of bacterium *E. coli*, (EC) with surfactants and the mixed molecular weight egg membrane peptide, Mx, all at the concentration of 1 wt % (as described in Example 11). The surfactant and polypeptide nomenclatures are indicated in the Materials section.
Figure 16:
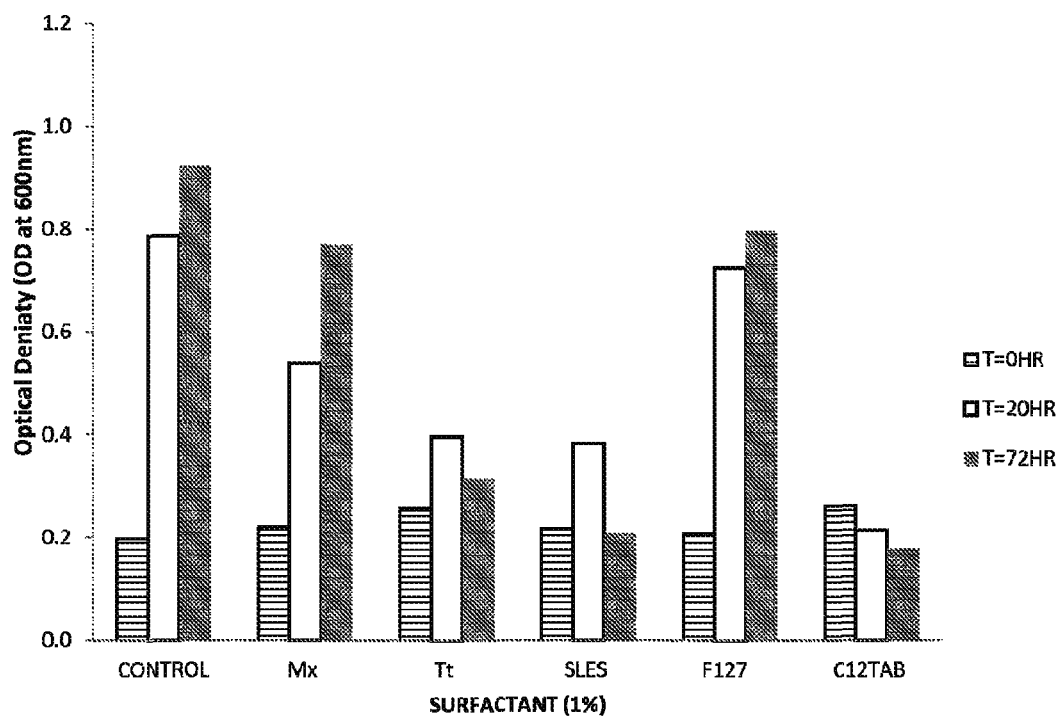
FIG. 16 Interactions of bacterium *S. aureus*, (SA) with surfactants and the mixed molecular weight egg membrane peptide, Mx, all at the concentration of 1 wt % (as described in Example 11). The surfactant and polypeptide nomenclatures are indicated in the Materials section.

The results below are shown for selected surfactants against *E. coli*, (EC) in FIG. 15 and *S. aureus*, (SA) in FIG. 16, respectively. The cationic surfactant C12TAB has significant antibacterial activity against both SA and EC. Even

TABLE 6

MTT results for fibroblasts Adult (HDFa) cells in culturing systems containing surfactants at 1% in concentration over three days. Low MTT readings indicate low viability. Changes in relative MTT readings indicate varying cell viabilities against time and peptide concentration. The surfactant and polypeptide nomenclatures are indicated previously in the Materials section.

| | Surf | | | | | | | | | | | | |
|---|---|---|---|---|---|---|---|---|---|---|---|---|---|
| | C12E5 | C12E6 | SDS | SL | Mx | Bx | P123 | F127 | Tt | SLES | CMEA | SILK | C12TAB |
| | Conc | | | | | | | | | | | | |
| | 0.50% | 1% | 1% | 1% | 1% | 1% | 1% | 1% | 1% | 1% | 1% | 1% | 1% |
| Day 1 | 0.01 | 0.01 | 0.01 | 1.23 | 1.30 | 0.21 | 0.09 | 0.81 | 0.01 | 0.00 | 0.00 | 1.03 | 0.00 |
| Day 2 | 0.01 | 0.01 | 0.01 | 0.82 | 0.95 | 0.12 | 0.06 | 0.78 | 0.00 | 0.00 | 0.00 | 0.75 | 0.00 |
| Day 3 | 0.01 | 0.01 | 0.01 | 0.80 | 1.07 | 0.16 | 0.14 | 0.75 | 0.00 | 0.00 | 0.00 | 0.85 | 0.00 | after 72 hours there was no growth of bacteria. In contrast, both Tt and SLES show some antibacterial influence but to lesser extent than C12TAB. In comparison, the non-ionic PLURONIC F127 and the mixed molecular weight egg peptide Mx showed no significant antibacterial activity.

Example 12

Antibacterial Activities from Peptide-Surfactant/Polymer Mixtures

The antibacterial activities of the designed short peptides in the presence of selected surfactants were investigated to determine if the peptides would sustain their antibacterial performance when surfactants are present. Bacteria E. coli, (EC) and S. aureus, (SA) were grown in LB media at 37° C. with continuous shaking for 24 hours. The bacterial concentrations were then adjusted such that the absorbance at 600 (A600) was controlled to ca 0.2 unit. The bacteria suspensions with the peptides were incubated in 96-well tissue culture plates. The total medium volume in each well was 2004. Concentrations of 25, 50 and 100 µM were used for each of the seven peptides and ampicillin. Controls used were (i) media only, (ii) media with bacteria only and (iii) bacteria with media containing peptides at a particular concentration. These were run alongside the peptide+bacteria and selected surfactant mixed suspensions. Measurements were taken at time t=0, t=20 and t=72 hours using optical density cell plate reader. Surfactants were added such that the final concentration was 1% within the wells.

TABLE 7

Antibacterial activities of the seven peptides and ampicillin against the Gram-negative bacteria E. coli, (EC) in the presence of selected surfactant and polymer additives. For each system ofantibacterial peptides at T = 0 hour and T = 20 hour the "Control" value refers to the bacterial growth without peptide or surfactant. For comparison, the value for bacteria with peptide but no surfactant is also given in the row labelled "no surf". The surfactant and polypeptide nomenclatures are indicated previously in the Materials section.

| | | G2 | | | G3 | | | G4 | | |
|---|---|---|---|---|---|---|---|---|---|---|
| Control | 25 µM | 50 µM | 100 µM | 25 µM | 50 µM | 100 µM | 25 µM | 50 µM | 100 µM | |
| | | | | | | | | | | T = 0 HOUR |
| 0.20 | 0.19 | 0.18 | 0.16 | 0.16 | 0.15 | 0.18 | 0.20 | 0.24 | 0.29 | NO SURF |
| | 0.18 | 0.15 | 0.13 | 0.12 | 0.14 | 0.18 | 0.20 | 0.24 | 0.30 | Mx |
| | 0.17 | 0.14 | 0.13 | 0.11 | 0.11 | 0.14 | 0.13 | 0.14 | 0.23 | Tt |
| | 0.09 | 0.08 | 0.09 | 0.10 | 0.07 | 0.08 | 0.07 | 0.09 | 0.12 | SLES |
| | 0.20 | 0.19 | 0.16 | 0.16 | 0.13 | 0.14 | 0.20 | 0.21 | 0.33 | F127 |
| | 0.31 | 0.32 | 0.28 | 0.29 | 0.28 | 0.27 | 0.35 | 0.37 | 0.23 | C12TAB |
| | | | | | | | | | | T = 20 HOUR |
| 0.95 | 0.79 | 0.70 | 0.64 | 0.65 | 0.56 | 0.20 | 0.31 | 0.25 | 0.28 | NO SURF |
| | 0.63 | 0.43 | 0.35 | 0.37 | 0.34 | 0.14 | 0.30 | 0.19 | 0.18 | Mx |
| | 0.28 | 0.18 | 0.20 | 0.06 | 0.06 | 0.06 | 0.06 | 0.08 | 0.09 | Tt |
| | 0.54 | 0.52 | 0.45 | 0.28 | 0.06 | 0.14 | 0.34 | 0.08 | 0.07 | SLES |
| | 0.81 | 0.88 | 0.80 | 0.81 | 0.68 | 0.50 | 0.45 | 0.31 | 0.30 | F127 |
| | 0.26 | 0.25 | 0.22 | 0.22 | 0.20 | 0.18 | 0.23 | 0.24 | 0.20 | C12TAB |

| | | AMPCIL | | | GO | | | GKI | | |
|---|---|---|---|---|---|---|---|---|---|---|
| Control | 25 µM | 50 µM | 100 µM | 25 µM | 50 µM | 100 µM | 25 µM | 50 µM | 100 µM | |
| | | | | | | | | | | T = 0 HOUR |
| 0.20 | 0.20 | 0.20 | 0.19 | 0.14 | 0.15 | 0.16 | 0.14 | 0.16 | 0.19 | NO SURF |
| | 0.21 | 0.20 | 0.20 | 0.14 | 0.15 | 0.16 | 0.14 | 0.16 | 0.19 | Mx |
| | 0.22 | 0.15 | 0.14 | 0.13 | 0.12 | 0.11 | 0.10 | 0.11 | 0.14 | Tt |
| | 0.22 | 0.18 | 0.15 | 0.10 | 0.08 | 0.06 | 0.09 | 0.07 | 0.08 | SLES |
| | 0.20 | 0.20 | 0.17 | 0.13 | 0.13 | 0.14 | 0.13 | 0.14 | 0.19 | F127 |
| | 0.27 | 0.26 | 0.27 | 0.20 | 0.20 | 0.20 | 0.15 | 0.24 | 0.23 | C12TAB |
| | | | | | | | | | | T = 20 HOUR |
| 0.98 | 0.20 | 0.16 | 0.16 | 0.54 | 0.43 | 0.11 | 0.49 | 0.14 | 0.15 | NO SURF |
| | 0.32 | 0.28 | 0.25 | 0.14 | 0.15 | 0.12 | 0.40 | 0.18 | 0.15 | Mx |
| | 0.09 | 0.07 | 0.07 | 0.06 | 0.06 | 0.06 | 0.06 | 0.07 | 0.09 | Tt |
| | 0.08 | 0.08 | 0.06 | 0.06 | 0.06 | 0.05 | 0.11 | 0.06 | 0.06 | SLES |
| | 0.15 | 0.13 | 0.14 | 0.66 | 0.59 | 0.47 | 0.51 | 0.32 | 0.14 | F127 |
| | 0.27 | 0.26 | 0.26 | 0.20 | 0.20 | 0.20 | 0.15 | 0.21 | 0.16 | C12TAB |

| | | GIK | | | GL | | |
|---|---|---|---|---|---|---|---|
| Control | 25 µM | 50 µM | 100 µM | 25 µM | 50 µM | 100 µM | |
| | | | | | | | T = 0 HOUR |
| 0.20 | 0.14 | 0.14 | 0.15 | 0.19 | 0.20 | 0.24 | NO SURF |
| | 0.15 | 0.15 | 0.16 | 0.18 | 0.19 | 0.24 | Mx |
| | 0.11 | 0.10 | 0.10 | 0.13 | 0.11 | 0.09 | Tt |
| | 0.07 | 0.07 | 0.07 | 0.10 | 0.08 | 0.08 | SLES |

TABLE 7-continued

Antibacterial activities of the seven peptides and ampicillin against the
Gram-negative bacteria E. coli, (EC) in the presence of selected surfactant and polymer
additives. For each system of antibacterial peptides at T = 0 hour and T = 20 hour the "Control"
value refers to the bacterial growth without peptide or surfactant. For comparison, the value
for bacteria with peptide but no surfactant is also given in the row labelled "no surf". The
surfactant and polypeptide nomenclatures are indicated previously in the Materials section.

|      |      | 0.12 | 0.12 | 0.13 | 0.19 | 0.18 | 0.22 | F127 |
|------|------|------|------|------|------|------|------|------|
|      |      | 0.21 | 0.24 | 0.20 | 0.21 | 0.22 | 0.15 | C12TAB |
|      |      |      |      |      |      |      |      | T = 20 HOUR |
| 0.95 | 0.54 | 0.35 | 0.14 | 0.55 | 0.49 | 0.46 | NO SURF |
|      | 0.48 | 0.37 | 0.15 | 0.40 | 0.27 | 0.25 | Mx |
|      | 0.08 | 0.08 | 0.08 | 0.06 | 0.06 | 0.05 | Tt |
|      | 0.42 | 0.21 | 0.06 | 0.30 | 0.07 | 0.27 | SLES |
|      | 0.62 | 0.45 | 0.37 | 0.54 | 0.60 | 0.55 | F127 |
|      | 0.18 | 0.18 | 0.12 | 0.17 | 0.16 | 0.10 | C12TAB |

The main outcome of the results indicates that no adverse effect of adding the surfactants to peptides occur with respect to antibacterial activity. In fact, all the selected surfactants and polymers improve the antibacterial activity of the peptides compared to the peptides alone, except for the pluronic F127. This surface active polymer seemed to reduce antibacterial effect or in other cases resulted in no improvement when compared to the peptides alone. In contrast, it is interesting to note that the mixed molecular weight egg polypeptide Mx seemed to enhance the antibacterial activity of the peptides, in particular when it was mixed with GO and G3. Note that Mx was found to have no significant antibacterial activity on its own. However, the antibacterial improvement by addition of Mx was not apparent for ampicillin, suggesting that for this antibiotic the mechanism for antibacterial activity may not be the same as that for the peptides. Similar results were observed with the Gram-positive bacteria S. aureus, (SA).

Example 13

Co-Culture of Cells with Bacteria and Surfactants/Polymers

Fibroblasts cells, Neonatal (HDFn) and Adult (HDFa), were grown in antibiotic free medium until greater than 80% confluent. Bacteria E. coli, (EC) and S. aureus, (SA) were grown in LB media at 37° C. with continuous shaking for 24 hours. The bacterial concentration was then adjusted such that the absorbance at 600 (A600) was set to ca 0.2 unit. Four peptides were selected (G4, GO, GIK and GKI) at a final concentration of 50 µM. The only surfactant/polymer used here was Mx at a 1% final concentration.

The cells were then harvested and seeded into micro well plate at cell densities of 5000 cells/well in a volume 100 µL of medium. After 24 hour incubation the culture medium was replaced with fresh medium containing an appropriate amount of the peptide, bacteria and also the selected surface active polypeptide for investigation. Controls were run with (i) cells only, (ii) cells with peptide and (iii) cells with peptide and bacteria. After 1 hour incubation the cells were analysed by visual observation through a microscope.

The results showed relatively similar fibroblast shape but some cell detachment for wells with cells and peptide when compared to the wells with cells only. The wells containing cells with peptide+bacteria had more detachment of cells than the wells with cells and peptide only. In contrast, for wells with cells, peptides, bacteria and the surface active polypeptide Mx the fibroblast shape was similar to that of the wells with the cells alone. This was apparent for both Neonatal (HDFn) and Adult (HDFa) in peptide GO and GKI but to a lesser extent in GIK and G4. This experiment shows that addition of surface active egg membrane polypeptide helps protect mammalian cells against the combined effects of bacterial attack and influence of antibacterial peptides associated with their selectivity.

On the other hand, inhibitions of bacterial growth were similar to or slightly better than the cases without the Mx polypeptides.

Example 14

Figure 17:
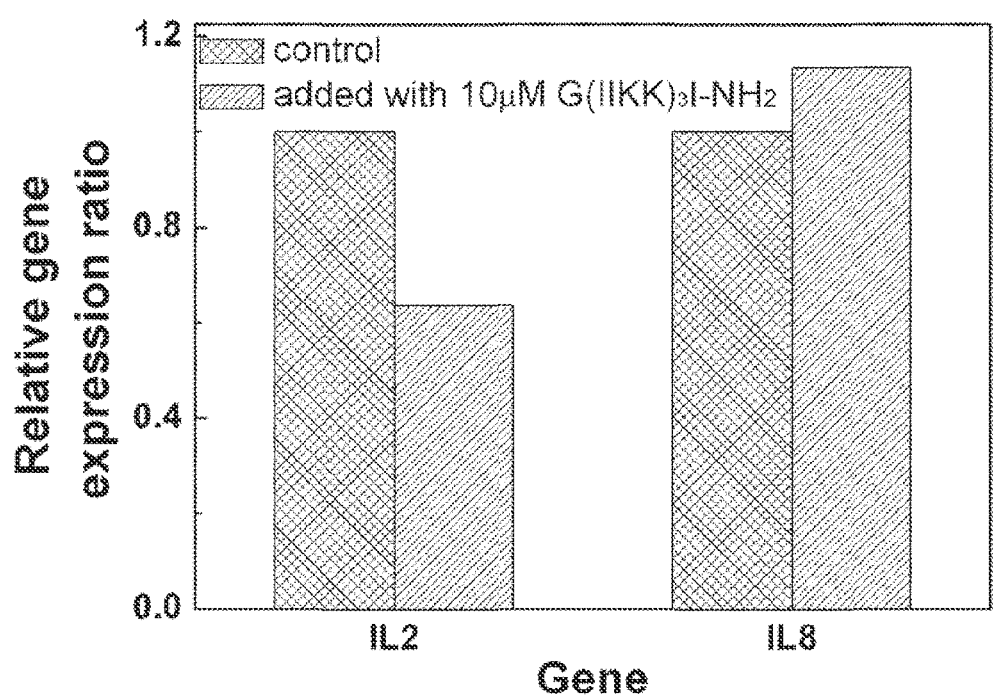
FIG. 17—Gene transcription levels of the cytokine genes IL2 and IL8 of lymphocytes treated with 10 μM G(IIKK)$_3$ I-NH$_2$ (SEQ ID NO: 3). The gene transcriptional levels were tested by RT-PCR.

Assessment of Non-Specific Immune Responses Through Examining Cytokines IL2 and IL8 Gene Transcriptions Natural antibacterial peptides isolated from living organisms are very limited in clinical use because of their high production cost, high hemolysis and possible immunological effects [Papo and Shai]. Apart from low production cost and low hemolytic action through high cell selectivity, the non-immunological effects of the designed helical peptides are also essential for developing their potential applications. The transcriptional levels of cytokine genes including IL2 and IL8 of human lymphocytes are widely used for the assessment of potential non-specific immune responses as a result of administration of an ingredient in formulated products such as in personal care or therapeutics. The two cytokine genes are regarded as the major immune system signal molecules that are able to respond to microbial infection and discriminate foreign molecules (non-self) and the body's own cells and molecules (self) in the human body [De Groote et al.; Feghali and Wright]. As a result, high expression of the two genes typically induces acute and chronic inflammation, causing potential health complications. In the context of this, the transcriptional responses of IL2 and IL8 were analyzed using RT-PCR assay, after their treatment with peptide G3 (G(IIKK)$_3$I-NH$_2$ (SEQ ID NO: 3)). As shown in FIG. 17, the relative transcriptional levels of IL2 and IL8 of lymphocytes following the peptide incubation was lower or almost equal to that of control cells, indicating that the interaction of G(IIKK)$_3$I-NH$_2$ (SEQ ID NO: 3) with lymphocytes did not induce non-specific immunogenic responses of the organism.

Summary from Examples 8 to 14

The most effective antibacterial peptides were G4, GO, GKI and GIK, with active antibacterial concentrations ranging from 25 to 100 μM. These peptides have very low toxicity against 3T3 fibroblast cells and human dermal derived fibroblast cells at concentrations below 50 μM within the conditions investigated. As peptide concentrations increase, antibacterial performance mostly improves but there is small but noticeable rise in toxicity against these mammalian cells, indicating the weakening of their selectivity.

The antibacterial peptides do not cause any non-specific immune responses as judged from the assessment of transcriptional levels of cytokine genes (IL2 and IL8) of human lymphocytes. These peptides thus possess advantages over those directly derived from living organisms in cost (often in much longer sequences) and by avoiding the risk of immune complications.

Surfactants and surface active polymers are essential ingredients for skin care formulations, but their presence could diminish antibacterial effects of the peptides. It is hence essential to test the formulation compatibility when surface active species are incorporated. On the other hand, the current experimental protocol also allows the vigorous assessment of biocompatibility of the surfactants/polymers used. From the experimental studies undertaken, almost all popularly used surfactants and surface active polymers are toxic to the fibroblast cells tested. Anionic surfactants such as SDS, cationic ones such as C12TAB and non-ionic ones such as C12E6 all lyse fibroblast cells from the first hour upon their addition, depending on exact concentrations used. SLES, widely used in the current skincare formulations and widely regarded as being biocompatible, also showed high toxicity. In contrast, pluronic F127 showed far less toxicity than other surface active polymers tested.

Water soluble silk polypeptides showed little toxicity to the fibroblast cells, but because they are not very surface active, their suitability in product formulations needs to be further investigated.

Water soluble egg membrane polypeptides are highly compatible to the fibroblast cells. As highly surface active polypeptides, their presence did not undermine antibacterial performance. Instead, these polypeptides showed some enhancement of antibacterial activity. As peptides are good nutrients, their addition at the concentration around 1 wt % in the cell culture would promote cell viability and healthy growth. These polypeptides are thus ideal ingredients to provide good formulation compatibility and biocompatibility in skin and hair care formulations and any other formulated products where the combination of these properties is sought.

REFERENCES

Tossi, A.; Tarantino, C.; Romeo, D.; Eur J Biochem 1997, 250, 549-558.
Tossi, A.; Sandri, L.; Giangaspero, A. Bioplymers 2000, 55, 4-30.
Cruciani, R. A.; Barker, J. L.; Zasloff, M.; Chen, H. C.; Colamonici, O. Proc Natl Acad Sci 1991, 88, 3792-3796.
Wieprecht, T.; Dathe, M.; Beyermann, M.; Krause, E.; Maloy, W. L.; MacDonald, D. L.; Bienert, M. *Biochemistry* 1997, 36, 6124-6132.
Asthana, N.; Yadav, S. P.; Ghosh, J. K. *J Biol Chem* 2004, 279, 55042-55050.
Greenwood, D.; O'Grady, F. *J Infect Dis* 1970, 122, 465-471.
Takara, K.; Obata, Y.; Yoshikawa, E.; Kitada, N.; Sakaeda, T.; Ohnishi, N.; Yokoyama, T. *Cancer Chemoth Pharm* 2006, 58, 785-793.
Jullian, M.; Hernandez, A.; Maurras, A.; Puget, K.; Amblard, M.; Martinez, J.; Subra, G. *Tetrahedron Lett* 2009, 50, 260-263.
Dathe, M.; Nikolenko, H.; Meyer, J.; Beyermann, M.; Bienert, M. *FEBS Lett* 2001, 501, 146-150.
Papo, N.; Shai, Y. *Cell Mol Life Sci.* 2005, 62, 784-790.
De Groote, D.; Zangerle, P. F.; Gevaert, Y.; Fassotte, M. F.; Beguin, Y.; Noizat-Pirenne, F. et al. *Cytokine* 1992, 4, 239-248.
Feghali, C. A.; Wright, T. M. *Front Biosci* 1997, 2, d12-26.

The invention claimed is:

1. A peptide of formula I or II shown below

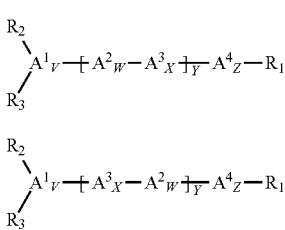

wherein:
$A^1$ is absent or an amino acid;
v is an integer selected from 0, 1, 2 or 3;
$A^2$ is independently for each occurrence a hydrophobic amino acid selected from isoleucine (I) and valine (V);
w is 2;
$A^3$ is a hydrophilic amino acid selected from lysine (K) and ornithine (O);
x is 2;
y is 2, 3 or 4;
$A^4$ is absent or an amino acid;
z is 0, 1, 2 or 3;
$R_1$ is a terminal substituent selected from OH, $NH_2$, (1-18C)alkyl, $N[(1-18C)alkyl]_2$ or NH(1-18C)alkyl; and
$R_2$ and $R_3$ are both independently selected from H, (1-18C)alkyl or (2-18C)acyl;
or a salt thereof;
wherein the peptide is capable of reducing the surface tension of water.

2. A peptide according to claim 1, wherein $A^2$ is isoleucine (I).

3. A peptide according to claim 1, wherein $A^3$ is lysine (K).

4. A peptide according to claim 1, wherein $A^2_w$ is II and/or $A^3_x$ is KK or OO.

5. A peptide according to claim 1, wherein v and/or z=1.

6. A peptide according to claim 1, wherein $A^1$ is glycine (G) and/or $A^4$ is isoleucine (I).

7. A peptide according to claim 1, wherein $R_1$ is $NH_2$.

8. A peptide according to claim 1, wherein $R_2$ and/or $R_3$ is H.

9. A peptide according to claim 1, selected from the group consisting of: G(IIKK) I-$NH_2$ (SEQ ID NO: 1); G(IIKK)$_2$I-$NH_2$ (SEQ ID NO: 2); G(IIKK)$_3$I-$NH_2$ (SEQ ID NO: 3); G(IIKK)$_4$I-$NH_2$ (SEQ ID NO: 4); G(LLKK)$_3$L-$NH_2$ (SEQ ID NO: 5); G(VVKK)$_3$V-$NH_2$ (SEQ ID NO: 6); G(IIOO)$_3$I-$NH_2$ (SEQ ID NO: 7); GKI(KKII)$_2$KII-$NH_2$ (SEQ ID NO: 8); and GIK(KKII)$_2$KII-$NH_2$ (SEQ ID NO: 9).

10. A peptide according to claim 1, comprising less than or equal to 20 amino acids.

11. The use of a peptide according to claim 1, as an antibacterial agent.

12. The use of a peptide according to claim 1, as a preservative.

13. The use of a peptide according to claim 1, as a surfactant.

14. An antibacterial composition comprising a peptide according to claim 1.

15. A personal care composition comprising a peptide according to claim 1.

16. A pharmaceutical composition comprising a peptide of formula I or II shown below

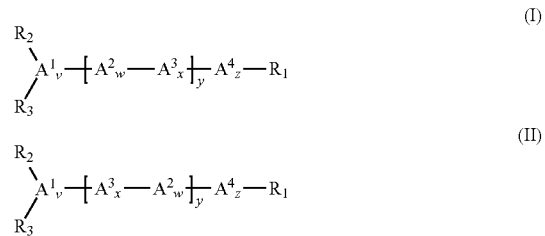

wherein:
$A^1$ is absent or an amino acid;
v is an integer selected from 0, 1, 2 or 3;
$A^2$ is a hydrophobic amino acid;
w is 2;
$A^3$ is a hydrophilic amino acid;
x is 2;
y is 2, 3 or 4;
$A^4$ is absent or an amino acid;
z is 0, 1, 2 or 3;
$R_1$ is a terminal substituent selected from OH, $NH_2$, (1-18C)alkyl, $N[(1-18C)alkyl]_2$ or NH(1-18C)alkyl; and
$R_2$ and $R_3$ are both independently selected from H, (1-18C)alkyl or (2-18C)acyl;
or a pharmaceutically acceptable salt thereof, in admixture with one or more pharmaceutically acceptable excipients; wherein the peptide is capable of reducing the surface tension of water.

17. A pharmaceutical composition according to claim 16 wherein in said peptide:
$A^2$ is independently for each occurrence a hydrophobic amino acid selected from isoleucine (I) and valine (V); and
$A^3$ is a hydrophilic amino acid selected from lysine (K) and ornithine (O).

18. A method of treating cancer comprising administering a therapeutically effective amount of a peptide of formula I or II shown below

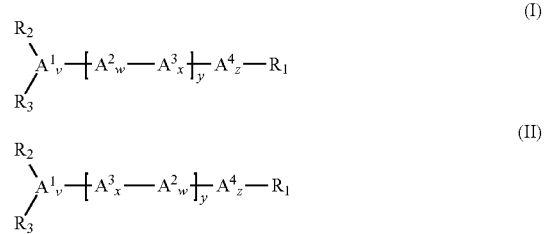

wherein:
$A^1$ is absent or an amino acid;
v is an integer selected from 0, 1, 2 or 3;
$A^2$ is a hydrophobic amino acid;
w is 2;
$A^3$ is a hydrophilic amino acid;
x is 2;
y is 2, 3 or 4;
$A^4$ is absent or an amino acid;
z is 0, 1, 2 or 3;

$R_1$ is a terminal substituent selected from OH, $NH_2$, (1-18C)alkyl, $N[(1-18C)alkyl]_2$ or NH(1-18C)alkyl; and $R_2$ and $R_3$ are both independently selected from H, (1-18C)alkyl or (2-18C)acyl;

or a pharmaceutically acceptable salt thereof, to an individual in need of such treatment;

wherein the peptide is capable of reducing the surface tension of water.

19. A method of treating cancer according to claim 18 wherein in said peptide:

$A^2$ is independently for each occurrence a hydrophobic amino acid selected from isoleucine (I) and valine (V); and $A^3$ is a hydrophilic amino acid selected from lysine (K) and ornithine (O).

20. A method of treating an infection comprising administering a therapeutically effective amount of a peptide of formula I or II shown below

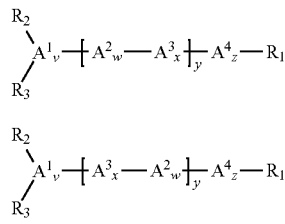

wherein:

$A^1$ is absent or an amino acid;

v is an integer selected from 0, 1, 2 or 3;

$A^2$ is a hydrophobic amino acid;

w is 2;

$A^3$ is a hydrophilic amino acid;

x is 2;

y is 2, 3 or 4;

$A^4$ is absent or an amino acid;

z is 0, 1, 2 or 3;

$R_1$ is a terminal substituent selected from OH, $NH_2$, (1-18C)alkyl, $N[(1-18C)alkyl]_2$ or NH(1-18C)alkyl; and $R_2$ and $R_3$ are both independently selected from H, (1-18C)alkyl or (2-18C)acyl;

or a pharmaceutically acceptable salt thereof, to an individual in need of such treatment;

wherein the peptide is capable of reducing the surface tension of water.

21. A method of treating an infection according to claim 20 wherein in said peptide:

$A^2$ is independently for each occurrence a hydrophobic amino acid selected from isoleucine (I) and valine (V); and $A^3$ is a hydrophilic amino acid selected from lysine (K) and ornithine (O).

* * * * *

```
                        SEQUENCE LISTING

<160> NUMBER OF SEQ ID NOS: 48

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 1

Gly Ile Ile Lys Lys Ile
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 2
```

Gly Ile Ile Lys Lys Ile Ile Lys Lys Ile
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 3

Gly Ile Ile Lys Lys Ile Ile Lys Lys Ile Ile Lys Lys Ile
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 4

Gly Ile Ile Lys Lys Ile Ile Lys Lys Ile Ile Lys Lys Ile Ile Lys
1               5                   10                  15

Lys Ile

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 5

Gly Leu Leu Lys Lys Leu Leu Lys Lys Leu Leu Lys Lys Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 6

Gly Val Val Lys Lys Val Val Lys Lys Val Val Lys Lys Val
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (4)..(5)
<223> OTHER INFORMATION: Ornithine
<220> FEATURE:
<221> NAME/KEY: MOD_RES
<222> LOCATION: (8)..(9)
<223> OTHER INFORMATION: Ornithine
<220> FEATURE:
<221> NAME/KEY: MOD_RES
<222> LOCATION: (12)..(13)
<223> OTHER INFORMATION: Ornithine
<220> FEATURE:
<223> OTHER INFORMATION: C-term amidated

<400> SEQUENCE: 7

Gly Ile Ile Xaa Xaa Ile Ile Xaa Xaa Ile Ile Xaa Xaa Ile
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 8

Gly Lys Ile Lys Lys Ile Ile Lys Lys Ile Ile Lys Ile Ile
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 9

Gly Ile Lys Lys Lys Ile Ile Lys Lys Ile Ile Lys Ile Ile
1               5                   10

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgccagggt acatggtggt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgtgcgtga cattaaggag                                               20

<210> SEQ ID NO 12
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggacttca gcagaaatct t                                              21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catgtcatca tccagtttgc                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
attatcgtcc aaaagtgtta                                                20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcacacaatc tacatcttct g                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgcagcagc ccttcaatta c                                              21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caatcctacc aaggcaacc                                                 19

<210> SEQ ID NO 18
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacattaacc tcaactcctg ccac                                            24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgttgatatt gctgattaag tccctg                                          26

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggaaggaac catctcactg tg                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agaaatcagg aaggctgcca ag                                              22

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(17)
<223> OTHER INFORMATION: This region may encompass 3-4 repeating "Ile
      Ile Lys Lys" units
<220> FEATURE:
<223> OTHER INFORMATION: C-term amidated

<400> SEQUENCE: 22

Gly Ile Ile Lys Lys Ile Ile Lys Lys Ile Ile Lys Lys Ile Ile Lys
1               5                   10                  15

Lys Ile

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MISC_FEATURE
<222> LOCATION: (2)..(17)
<223> OTHER INFORMATION: This region may encompass 1-4 repeating "Ile
      Ile Lys Lys" units
<220> FEATURE:
<223> OTHER INFORMATION: C-term amidated

<400> SEQUENCE: 23

Gly Ile Ile Lys Lys Ile Ile Lys Lys Ile Ile Lys Lys Ile Ile Lys
1               5                   10                  15

Lys Ile

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Ile Lys Lys
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ile His His
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ile Arg Arg
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Ornithine

<400> SEQUENCE: 27

Ile Ile Xaa Xaa
1

<210> SEQ ID NO 28
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Leu His His
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Leu Lys Lys
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Arg Arg
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Ornithine

<400> SEQUENCE: 31

Leu Leu Xaa Xaa
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Val His His
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 33

Val Val Lys Lys
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Val Arg Arg
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Ornithine

<400> SEQUENCE: 35

Val Val Xaa Xaa
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His His Ile Ile
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His His Leu Leu
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His His Val Val
1

```
<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Lys Ile Ile
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Lys Leu Leu
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Lys Val Val
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Ile Ile
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Leu Leu
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 44

Arg Arg Val Val
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ornithine

<400> SEQUENCE: 45

Xaa Xaa Ile Ile
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ornithine

<400> SEQUENCE: 46

Xaa Xaa Leu Leu
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ornithine

<400> SEQUENCE: 47

Xaa Xaa Val Val
1

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-aminohexanoic acid

<400> SEQUENCE: 48

Xaa Gly Ile Ile Lys Lys Ile Lys Lys Ile Ile Lys Lys Ile
1               5                   10                  15
```